(12) United States Patent
Iyer et al.

(10) Patent No.: US 12,279,953 B2
(45) Date of Patent: Apr. 22, 2025

(54) PROSTHETIC HEART VALVES

(71) Applicant: Laplace Interventional Inc., Plymouth, MN (US)

(72) Inventors: Ramji Iyer, Plymouth, MN (US); Lucas Tradd Schneider, Champlin, MN (US); Gunnar Paul Askegaard, Brainerd, MN (US)

(73) Assignee: Laplace Interventional Inc., Plymouth, MN (US)

( * ) Notice: Subject to any disclaimer, the term of this patent is extended or adjusted under 35 U.S.C. 154(b) by 0 days.

(21) Appl. No.: 18/768,710

(22) Filed: Jul. 10, 2024

(65) Prior Publication Data

US 2024/0358504 A1    Oct. 31, 2024

Related U.S. Application Data

(63) Continuation of application No. 18/428,630, filed on Jan. 31, 2024, now Pat. No. 12,059,346, which is a continuation of application No. 18/135,536, filed on Apr. 17, 2023, now Pat. No. 11,918,463, which is a continuation of application No. 17/993,573, filed on Nov. 23, 2022, now Pat. No. 11,672,655, which is a continuation of application No. 17/747,507, filed on May 18, 2022, now Pat. No. 11,510,777.

(60) Provisional application No. 63/308,657, filed on Feb. 10, 2022.

(51) Int. Cl.
 *A61F 2/24* (2006.01)
(52) U.S. Cl.
 CPC .......... *A61F 2/2418* (2013.01); *A61F 2/2427* (2013.01); *A61F 2/2436* (2013.01); *A61F 2/2412* (2013.01); *A61F 2210/0014* (2013.01); *A61F 2220/0008* (2013.01); *A61F 2230/0006* (2013.01); *A61F 2230/0008* (2013.01); *A61F 2250/0006* (2013.01); *A61F 2250/001* (2013.01); *A61F 2250/0069* (2013.01)

(58) Field of Classification Search
None
See application file for complete search history.

(56) References Cited

U.S. PATENT DOCUMENTS

| 5,824,069 A | 10/1998 | Lemole |
| 6,312,464 B1 | 11/2001 | Navia |
| 6,458,153 B1 | 10/2002 | Bailey et al. |

(Continued)

FOREIGN PATENT DOCUMENTS

WO    WO 2015/052570    4/2015

OTHER PUBLICATIONS

International Search Report and Written Opinion in International Appln. No. PCT/US2023/012615, mailed on Aug. 10, 2023, 25 pages.

(Continued)

*Primary Examiner* — Rebecca S Preston
(74) *Attorney, Agent, or Firm* — Fish & Richardson P.C.

(57) ABSTRACT

Some embodiments described herein include a heart valve replacement system that may be delivered to a targeted native heart valve site via one or more delivery catheters. In some embodiments, a prosthetic heart valve of the system includes structural features that securely anchor the prosthetic heart valve to the site of the native heart valve. Such structural features can provide robust migration resistance. In particular implementations, the prosthetic heart valves occupy a smaller delivery profile, thereby facilitating a smaller delivery catheter for advancement to the heart.

18 Claims, 18 Drawing Sheets

(56) References Cited

U.S. PATENT DOCUMENTS

| | | |
|---|---|---|
| 8,728,155 B2 | 5/2014 | Montorfano et al. |
| 9,393,110 B2 | 7/2016 | Levi et al. |
| 9,579,196 B2 | 2/2017 | Morriss |
| 9,681,951 B2 | 6/2017 | Ratz et al. |
| 10,213,307 B2 | 2/2019 | Dwork |
| 10,321,995 B1 | 6/2019 | Christianson |
| 10,583,000 B2 | 3/2020 | Ratz |
| 10,653,522 B1 | 5/2020 | Vidlund et al. |
| 10,779,936 B2 | 9/2020 | Pollak |
| 10,813,779 B2 | 10/2020 | Fleming, III et al. |
| 11,109,965 B2 | 9/2021 | Iyer et al. |
| 2005/0149181 A1 | 7/2005 | Eberhardt |
| 2007/0055356 A1 | 3/2007 | Eidenschink |
| 2010/0023046 A1 | 1/2010 | Heidner et al. |
| 2010/0161045 A1 | 6/2010 | Righini |
| 2010/0217382 A1 | 8/2010 | Chau et al. |
| 2010/0316830 A1 | 12/2010 | Hartley et al. |
| 2011/0137397 A1 | 6/2011 | Chau et al. |
| 2012/0083832 A1 | 4/2012 | Delaloye et al. |
| 2013/0211508 A1 | 8/2013 | Lane et al. |
| 2013/0325114 A1 | 12/2013 | McLean et al. |
| 2014/0207231 A1 | 7/2014 | Hacohen et al. |
| 2014/0222142 A1 | 8/2014 | Kovalsky et al. |
| 2014/0257467 A1 | 9/2014 | Lane et al. |
| 2014/0277390 A1 | 9/2014 | Ratz |
| 2014/0296969 A1 | 10/2014 | Tegels et al. |
| 2014/0296975 A1 | 10/2014 | Tegels et al. |
| 2014/0324164 A1 | 10/2014 | Gross et al. |
| 2014/0350669 A1 | 11/2014 | Gillespie et al. |
| 2015/0119981 A1 | 4/2015 | Khairkhahan et al. |
| 2015/0196390 A1 | 7/2015 | Ma et al. |
| 2015/0216653 A1 | 8/2015 | Freudenthal |
| 2015/0327994 A1 | 11/2015 | Morriss et al. |
| 2016/0158003 A1 | 6/2016 | Wallace et al. |
| 2016/0278922 A1 | 9/2016 | Braido et al. |
| 2017/0056166 A1 | 3/2017 | Ratz et al. |
| 2017/0071733 A1 | 3/2017 | Ghione et al. |
| 2017/0128199 A1 | 5/2017 | Gurovich et al. |
| 2017/0128208 A1 | 5/2017 | Christianson et al. |
| 2017/0216023 A1 | 8/2017 | Lane et al. |
| 2017/0216026 A1 | 8/2017 | Quill et al. |
| 2017/0325945 A1 | 11/2017 | Dale et al. |
| 2018/0000586 A1 | 1/2018 | Ganesan |
| 2018/0116798 A1 | 5/2018 | Perszyk |
| 2018/0303612 A1 | 10/2018 | Pasquino et al. |
| 2019/0008636 A1 | 1/2019 | Francis et al. |
| 2019/0029811 A1 | 1/2019 | Bishop et al. |
| 2019/0183639 A1 | 6/2019 | Moore |
| 2020/0179109 A1 | 6/2020 | Reimer |
| 2020/0237506 A1 | 7/2020 | Christianson et al. |
| 2020/0268512 A1 | 8/2020 | Mohl |
| 2021/0244535 A1 | 8/2021 | Iyer et al. |
| 2021/0346153 A1 | 11/2021 | Vietmeier et al. |
| 2021/0393401 A1 | 12/2021 | Iyer et al. |

OTHER PUBLICATIONS

International Preliminary Report on Patentability in International Appln. No. PCT/US2023/012615, mailed on Aug. 22, 2024, 8 pages.

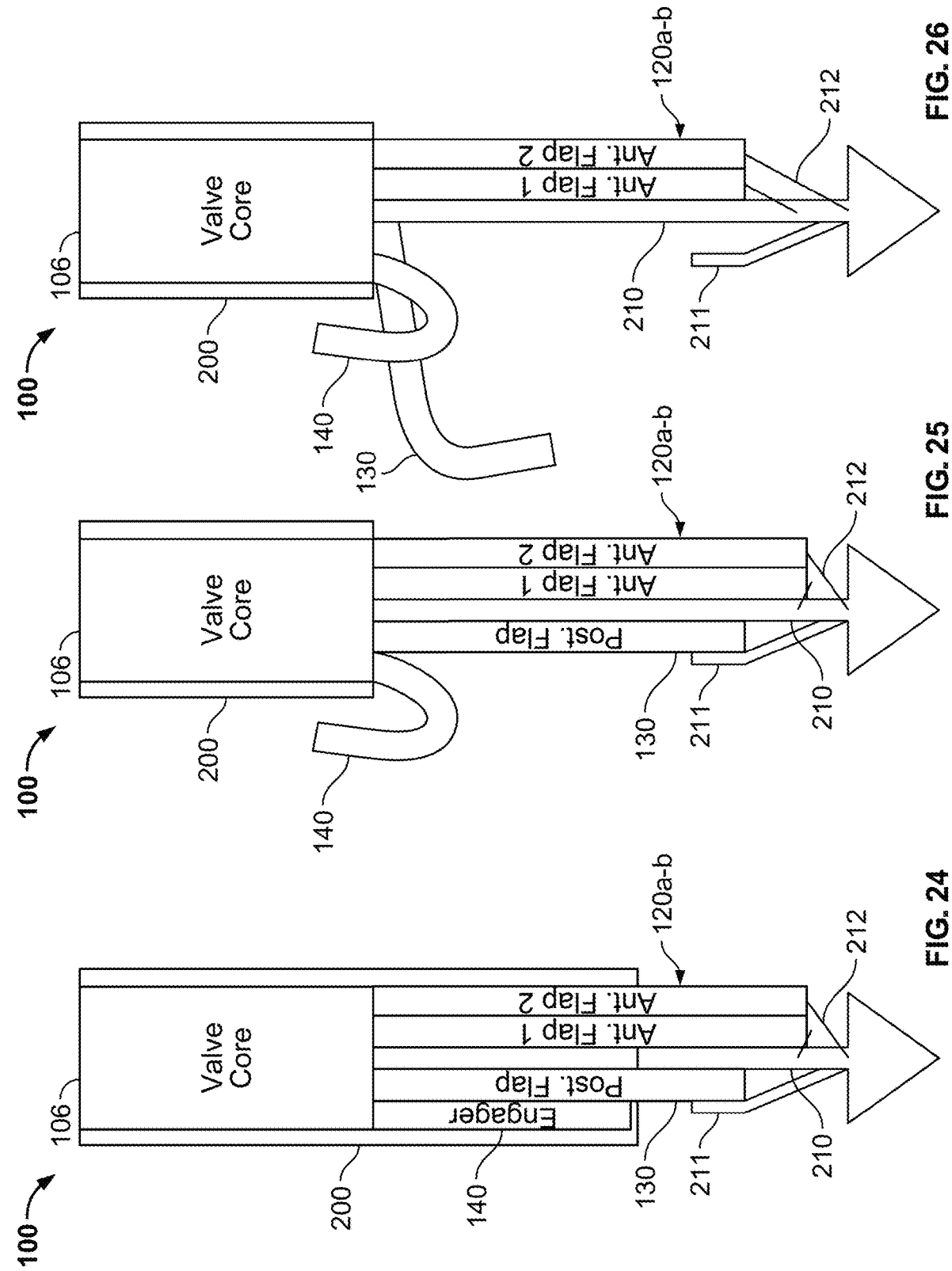

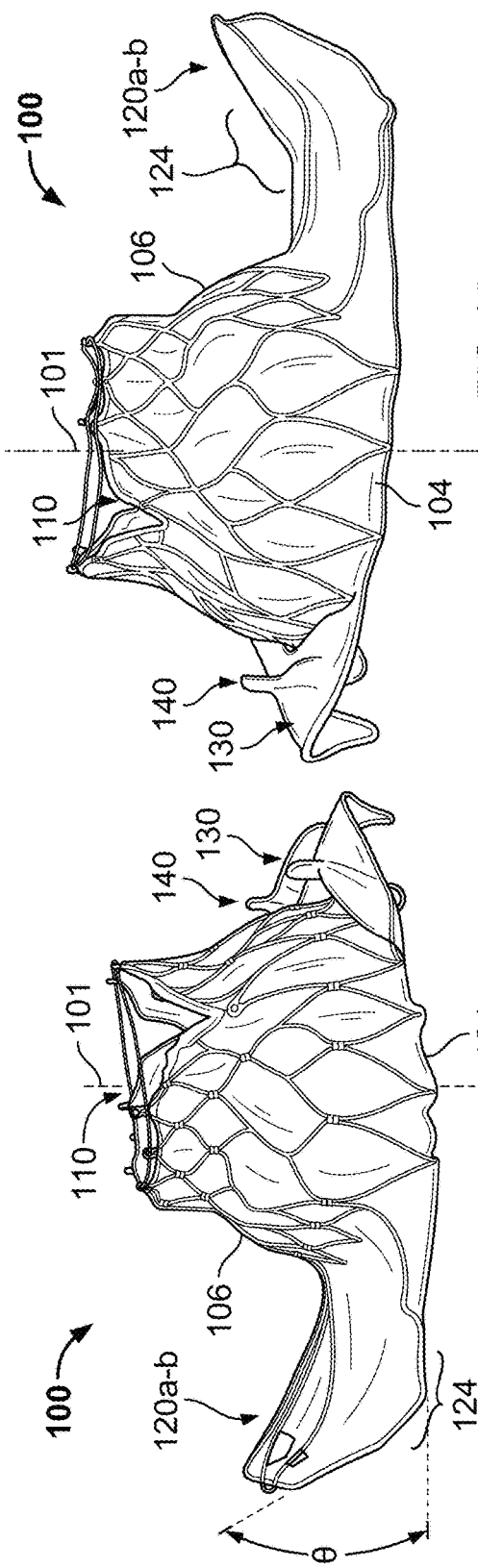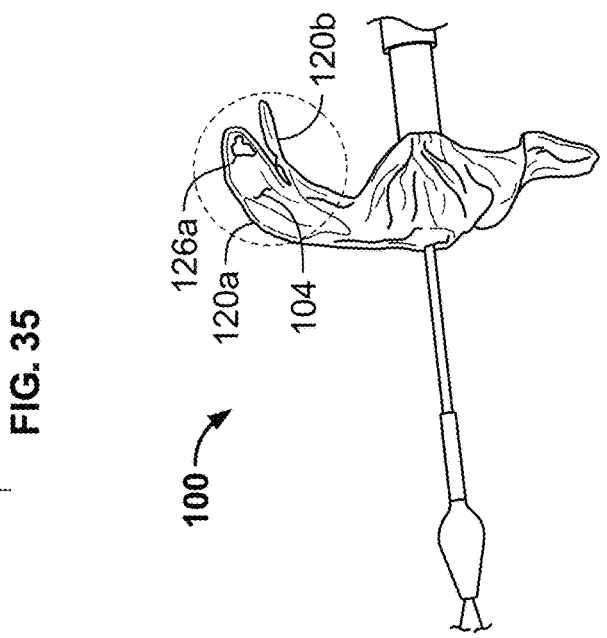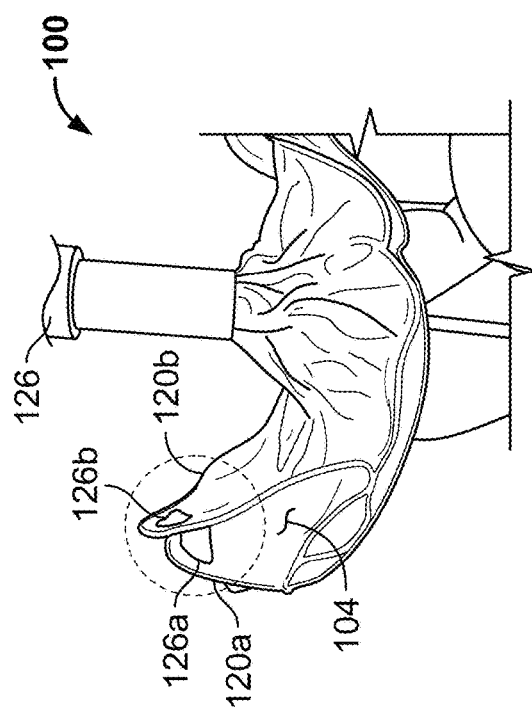

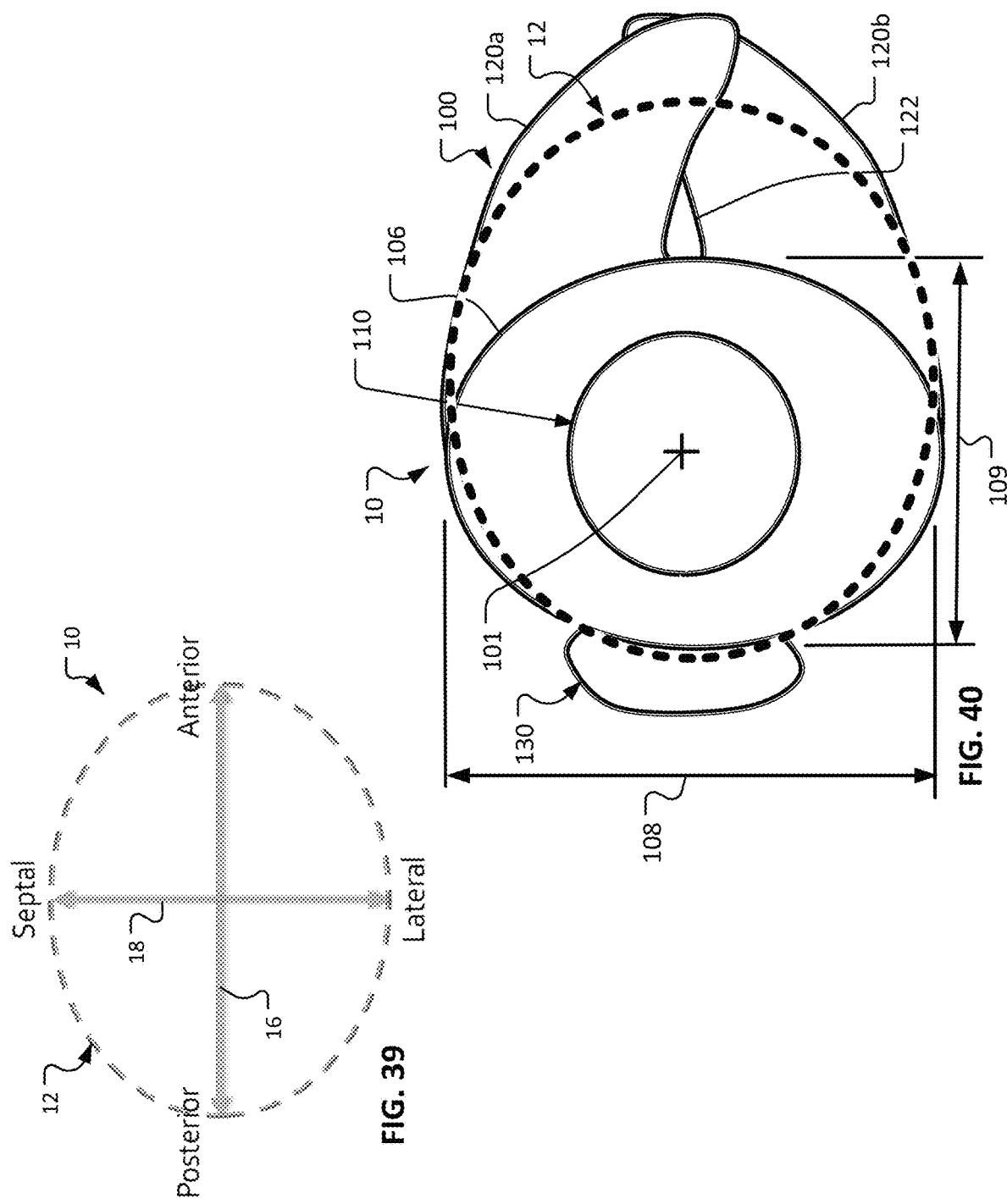

PROSTHETIC HEART VALVES

CROSS-REFERENCE TO RELATED APPLICATIONS

This application is a continuation of U.S. application Ser. No. 18/428,630 filed on Jan. 31, 2024, which is a continuation of U.S. application Ser. No. 18/135,536 filed on Apr. 17, 2023 (U.S. Pat. No. 11,918,463), which is a continuation of U.S. application Ser. No. 17/993,573 filed on Nov. 23, 2022 (U.S. Pat. No. 11,672,655), which is a continuation of U.S. application Ser. No. 17/747,507 filed on May 18, 2022 (U.S. Pat. No. 11,510,777), which claims the benefit of U.S. Provisional Application Ser. No. 63/308,657, filed Feb. 10, 2022. The disclosures of the prior applications are considered part of (and are incorporated by reference in) the disclosure of this application.

FIELD OF INVENTION

This disclosure generally relates to prosthetic heart valve systems. For example, this disclosure relates to transcatheter deliverable prosthetic heart valves that are adapted to be used to replace a sub-optimally functioning native heart valve, including but not limited to a tricuspid valve.

BACKGROUND

A human heart includes four types of heart valves that are arranged to ensure blood flow in specific directions: mitral, tricuspid, aortic and pulmonary valves. The aortic and pulmonary valves are semilunar valves, which are in the arteries leaving the heart, and prevent blood from flowing back into left ventricle and right ventricle respectively when closed. The mitral and tricuspid valves are atrio-ventricular valves, which are between the atria and the ventricles, and prevent blood from flowing back into left atrium and right atrium respectively when closed. Conditions of stenosis (when valve does not open fully) as well as regurgitation/insufficiency (when valve does not close properly resulting in leaks) are recognized as significant contributors to mortality and morbidity.

Some valve replacement systems include valve prostheses that are compressed into a delivery catheter, also referred to as transcatheter valves, so as to avoid open-heart surgery. Many transcatheter valve prostheses have a tubular frame that may or may not be axisymmetric, and include two or more leaflets. While these transcatheter valve prostheses can be compressed into a catheter, they may still require a large delivery system (for example, a required catheter size of 45 French). This is especially true in case of mitral valve replacement systems and tricuspid valve replacement systems, which often require valve prostheses with a larger footprint.

SUMMARY

Some embodiments described herein include a heart valve replacement system that may be delivered to a targeted native heart valve site via one or more delivery catheters. In some embodiments, a prosthetic heart valve of the system includes structural features that securely anchor the prosthetic heart valve to the site of the native heart valve. Such structural features can provide robust migration resistance. In particular implementations, the prosthetic heart valves occupy a smaller delivery profile, thereby facilitating a smaller delivery catheter for advancement to the heart.

In one aspect, this disclosure is directed to a prosthetic heart valve embodiment. The prosthetic heart valve can have a deployed configuration that includes a main body comprising an inflow end portion and an outflow end portion; an occluder defining an axis extending between the inflow end and outflow end portions and comprising valve leaflets attached to the main body in an arrangement that: (i) allows blood flow through the occluder in a direction from the inflow end portion toward the outflow end portion and (ii) prevents blood flow through the occluder in a direction from the outflow end portion toward the inflow end portion; a posterior flap extending transversely to the axis and away from the outflow end portion of the main body; and a leaflet engagement member extending from the main body in a same direction as the posterior flap, a portion of the leaflet engagement member extending toward the inflow end portion and terminating at a free end.

Such a prosthetic heart valve may optionally include one or more of the following features. The area of the main body that the leaflet engagement member extends from may be the outflow end portion or a mid-body portion located between the inflow end and outflow end portions. The portion of the leaflet engagement member may extend along an outside of the main body and may be spaced apart from the main body. The posterior flap may extend laterally farther away from the main body than the leaflet engagement member. The leaflet engagement member may include a U-shaped wire loop. The leaflet engagement member may be a first leaflet engagement member that terminates at a first free end, and the prosthetic heart valve may also include a second leaflet engagement member extending in the direction from the outflow end portion toward the inflow end portion and terminating at a second free end. The prosthetic heart valve may also include an anterior flap extending transversely to the axis and away from the outflow end portion of the main body in a direction opposite of the posterior flap. The anterior flap may be a first anterior flap, and the prosthetic heart valve may also include a second anterior flap extending transversely to the axis and away from the outflow end portion of the main body in a same direction as the first anterior flap. Portions of the first anterior flap and the second anterior flap may overlap each other when the prosthetic heart valve is deployed. An open space may be defined between the first anterior flap and the second anterior flap when the prosthetic heart valve is deployed.

In another aspect, another prosthetic heart valve embodiment is disclosed herein that includes a main body comprising a first end, a second end that is opposite of the first end, and an occluder having valve leaflets; a first anterior flap extending laterally from the second end of the main body; and a second anterior flap extending laterally from the second end of the main body in a same direction as the first anterior flap. The first anterior flap and the second anterior flap can each include a mid-body portion that is bent at an angle that directs terminal end portions of each of the first anterior flap and the second anterior flap partially toward the first end of the main body.

Such a prosthetic heart valve can optionally include one or more of the following features. The angle may be between 20° and 60°. Portions of the first anterior flap and the second anterior flap may overlap each other when the prosthetic heart valve is deployed. The prosthetic heart valve may also include a posterior flap extending laterally away from the second end of the main body in a direction laterally opposite of the first and second anterior flaps. The posterior flap may include a mid-body portion that is bent to direct a terminal end portion of the posterior flap away from the first end of the main body.

In another aspect, another prosthetic heart valve embodiment is disclosed herein that includes a main body comprising a first end, a second end that is opposite of the first end, and an occluder having valve leaflets, the occluder defining an axis extending between the first and second ends; a first anterior flap extending transversely to the axis and away from the second end of the main body; a second anterior flap extending transversely to the axis and away from the second end of the main body in a same direction as the first anterior flap; and a covering attached to the first and second anterior flaps. The covering defines a first opening through a terminal end portion of the first anterior flap, and a second opening through a terminal end portion of the second anterior flap.

Such a prosthetic heart valve can optionally include one or more of the following features. The first anterior flap and the second anterior flap may each include a mid-body portion that is bent at an angle that directs the terminal end portions of each of the first anterior flap and the second anterior flap partially toward the first end of the main body. The angle may be between 20° and 60°. Portions of the first anterior flap and the second anterior flap may overlap each other when the prosthetic heart valve is deployed. An open space may be defined between the first anterior flap and the second anterior flap when the prosthetic heart valve is deployed.

In another aspect, another prosthetic heart valve embodiment is disclosed herein that includes a main body comprising an inflow end portion and an outflow end portion, a transverse cross-section of the main body having an oval shaped outer profile that defines a major diameter; an occluder extending between the inflow end and outflow end portions and comprising valve leaflets attached to the main body in an arrangement that:

(i) allows blood flow through the occluder in a direction from the inflow end portion toward the outflow end portion and (ii) prevents blood flow through the occluder in a direction from the outflow end portion toward the inflow end portion, the occluder having a circular cross-sectional shape; an anterior flap extending transversely to the major diameter and away from the outflow end portion of the main body; and a posterior flap extending transversely to the major diameter and away from the outflow end portion of the main body in a direction opposite of the anterior flap.

Such a prosthetic heart valve can optionally include one or more of the following features. The prosthetic heart valve may also include a leaflet engagement member extending from the main body. A portion of the leaflet engagement member may extend toward the inflow end portion and terminating at a free end. The leaflet engagement member may extend in a same direction as the posterior flap. The anterior flap is a first anterior flap, and the prosthetic heart valve may also include a second anterior flap extending transversely to the major diameter and away from the outflow end portion of the main body in a same direction as the first anterior flap.

Any of the prosthetic heart valves described herein may optionally include one or more of the following additional features. In some embodiments, portions of the first anterior flap and the second anterior flap overlap each other. The prosthetic tricuspid valve may also include a posterior flap extending laterally from the end of the main body in an opposite direction as the first and second anterior flaps. In some embodiments, the first and second anterior flaps extend farther laterally than the posterior flap. In particular embodiments, the first and second anterior flaps in combination are wider than the posterior flap. A framework of the prosthetic tricuspid valve (that comprises the main body, the first and second anterior flaps, and the posterior flap) may be made of a single, unitary material that was cut and expanded. In some embodiments, a distal tip portion of the posterior flap extends along an axis that is at a non-zero angle relative to a portion of the posterior flap that extends directly from the main body. In some examples, having the portions of the first anterior flap and the second anterior flap that overlap each other increases a bending resistance of the first anterior flap and the second anterior flap in combination as compared to the first anterior flap and the second anterior flap individually. Having the portions of the first anterior flap and the second anterior flap as separate members can configure the prosthetic tricuspid valve to have a pacemaker lead pass through the prosthetic tricuspid valve between the first and second anterior flaps. The prosthetic tricuspid valve may also include one or more additional anterior flaps extending laterally from the end of the main body in the same direction as the first and second anterior flaps. The prosthetic tricuspid valve may also include two or more posterior flaps extending laterally from the end of the main body in an opposite direction as the first and second anterior flaps.

A deployment system may be used in combination with the prosthetic tricuspid valve. Such a deployment system may include a sheath catheter defining a first lumen, an outer proximal catheter slidably disposed within the first lumen and defining a second lumen, and an inner distal catheter slidably disposed within the second lumen. The prosthetic tricuspid valve may be disposed within the first lumen in a low profile delivery configuration and may be releasably attached to one or both of the outer proximal catheter and the inner distal catheter. In some embodiments, the main body is releasably attached to outer proximal catheter, and/or the first and second anterior flaps are releasably attached to the inner distal catheter. The prosthetic tricuspid valve may also include a posterior flap extending laterally from the end of the main body in an opposite direction as the first and second anterior flaps. The posterior flap may be disposed within the first lumen while not being directly attached to the deployment system. In some embodiments, the first and second anterior flaps are individually releasably attached to the inner distal catheter.

In another aspect, this disclosure is directed to a method of treating a deficiency of a native tricuspid valve. The method includes implanting a prosthetic tricuspid valve in the native tricuspid valve. The prosthetic tricuspid valve may be configured in any of the arrangements described herein. In some embodiments, the implanting comprises: (i) positioning the posterior flap in a posterior region of a right ventricle, and (ii) positioning the first and second anterior flaps in a right ventricular outflow tract ("RVOT") of the right ventricle.

BRIEF DESCRIPTION OF FIGURES

FIG. 24 schematically shows an example prosthetic heart valve contained within a delivery sheath.

FIG. 25 schematically shows a first stage of deployment of the prosthetic heart valve from the delivery sheath of FIG. 24.

FIG. 26 schematically shows a second stage of deployment of the prosthetic heart valve from the delivery sheath of FIG. 24.

FIG. 34 is a first side view of another example prosthetic heart valve in accordance with some embodiments.

FIG. 35 is a second side view of the prosthetic heart valve of FIG. 34.

FIG. 36 is a first view of example anterior flaps of another example prosthetic heart valve in accordance with some embodiments.

FIG. 37 is a second view of the example anterior flaps of FIG. 36.

FIG. 39 schematically illustrates an example shape of a tricuspid valve annulus in accordance with some native anatomies.

FIG. 40 schematically illustrates an example prosthetic heart valve in accordance with some embodiments within the tricuspid valve annulus of FIG. 39.

DETAILED DESCRIPTION

Some embodiments described herein include a heart valve replacement system that may be delivered to a targeted native heart valve site via one or more delivery catheters. In some embodiments, a prosthetic heart valve of the system includes structural features that securely anchor the prosthetic heart valve to the site of the native heart valve. Such structural features can provide robust migration resistance. In particular implementations, the prosthetic heart valves occupy a smaller delivery profile, thereby facilitating a smaller delivery catheter for advancement to the heart.

Figure 1:
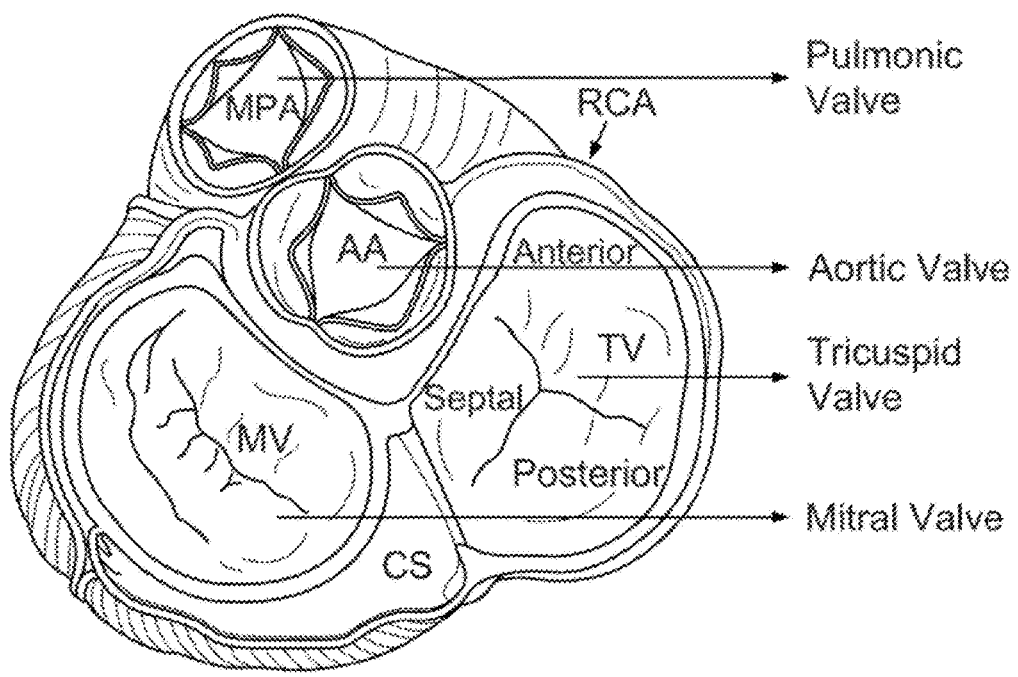
FIG. 1 shows a sectional view of a human heart including four heart valves (mitral valve, tricuspid valve, aortic valve, and pulmonary valve) that allow blood flow through specific pathways. The mitral and tricuspid valve are arranged to prevent backflow of blood into left atrium and right atrium respectively when the left and right ventricle contract respectively.
Figure 2:
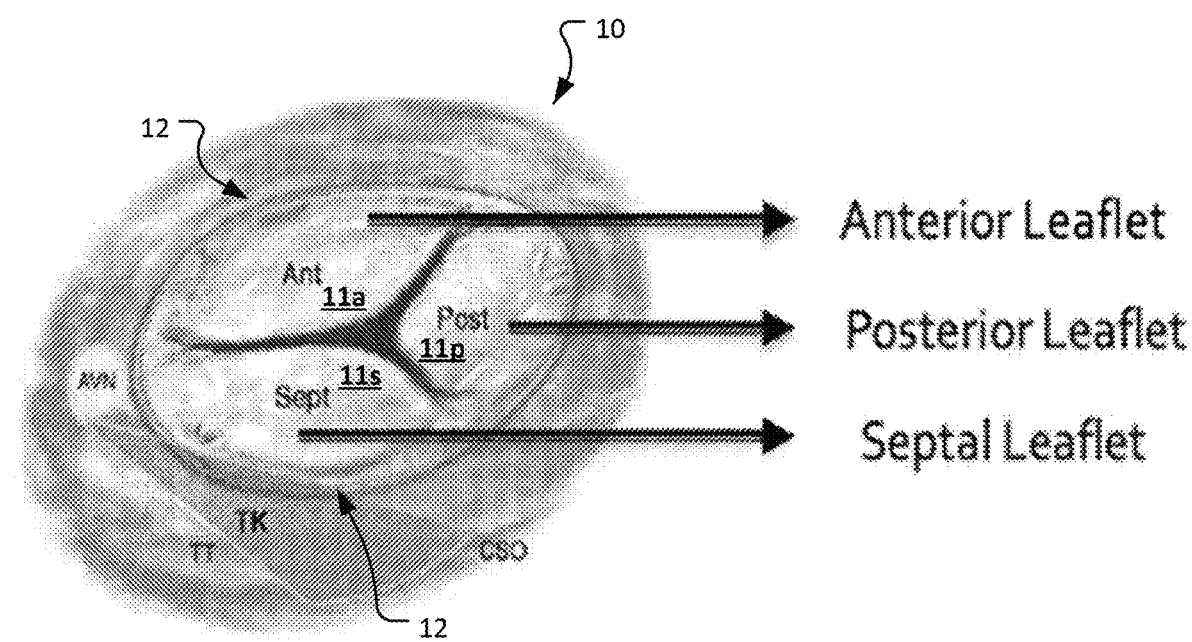
FIG. 2 shows a top view of the tricuspid valve of FIG. 1 and including three native leaflets: anterior, posterior and septal.

Referring to FIG. 1, the concepts described herein regarding the heart valve replacement systems can be implemented in prosthetic valve designs that are intended for use at any of the four heart valves that allow blood flow through a specific pathway: mitral valve, tricuspid valve, aortic valve and the pulmonary valve. FIG. 2 depicts, for example, a targeted site at a tricuspid valve 10 of the heart. The tricuspid valve 10 includes an anterior leaflet 11a, a posterior leaflet 11p, and a septal leaflet 11s, and an annulus 12. In some circumstances, the tricuspid valve 10 may undergo stenosis or anatomical changes that cause tricuspid regurgitation, such as instances in which the distance between the anterio-septal commissure and the anterio-posterior commissure of the native tricuspid valve increases with the progression of a diseased state due to dilation of the annulus 12 of the tricuspid valve 10.

Figure 3:
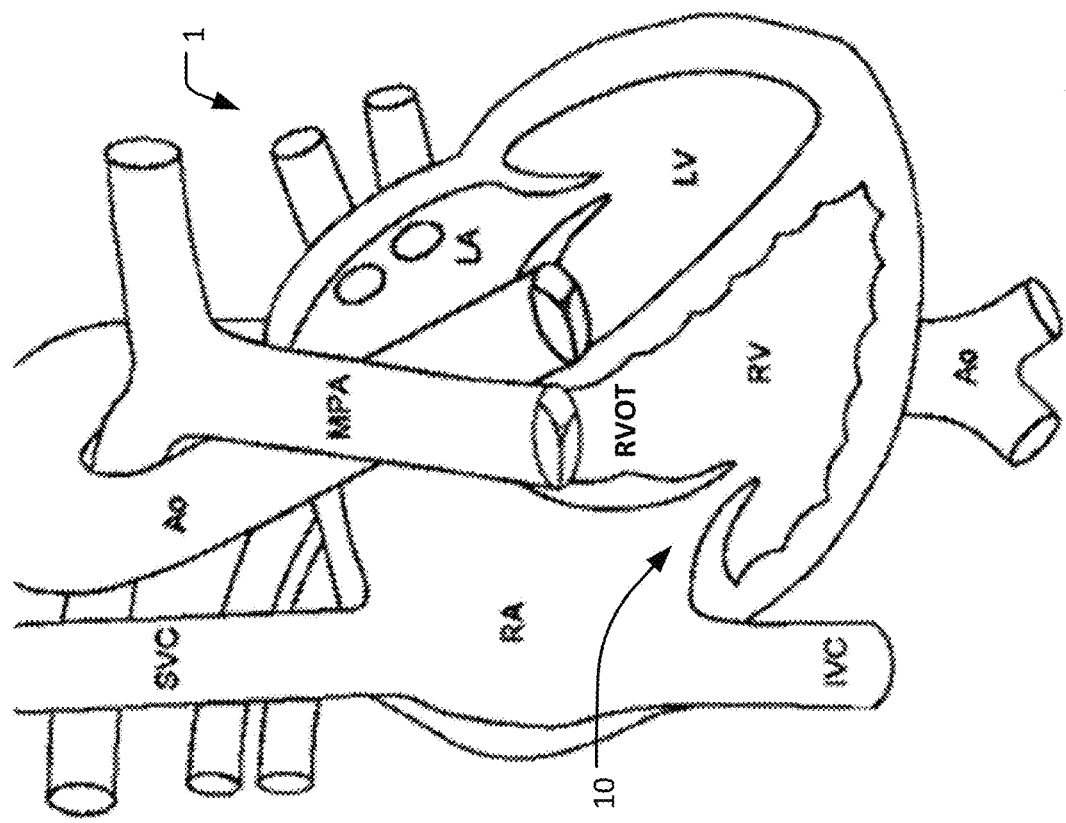
FIG. 3 shows another sectional view of a human heart including the four chambers (right atrium, right ventricle, left atrium, and left ventricle) and major conduits that deliver blood to the heart and transport blood away from the heart.

FIG. 3 illustrates a longitudinal sectional view of a human heart 1 that shows the four chambers (right atrium, right ventricle, left atrium, and left ventricle) and the major conduits that deliver blood to the heart 1 and transport blood away from the heart 1. The tricuspid valve 10 is located between the right atrium and the right ventricle. Blood flows from the right atrium to the right ventricle through the tricuspid valve 10. The blood exits the right ventricle and enters the main pulmonary artery ("MPA") via the RVOT that is adjacent to the tricuspid valve 10.

Figure 5:
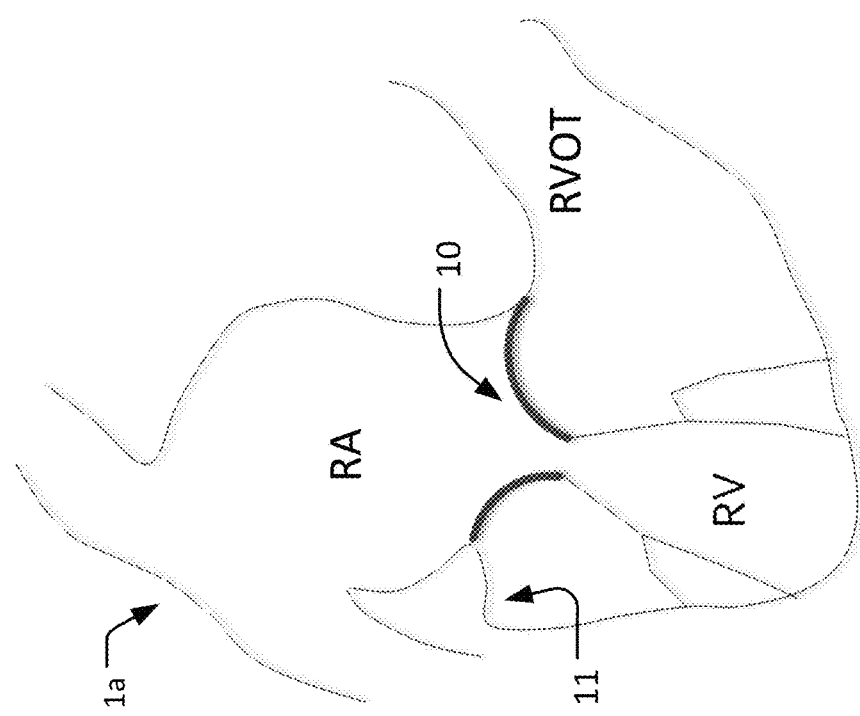
FIG. 5 shows another schematic view of the right side of the heart of FIG. 3, including the RA, RV, and RVOT, in accordance with some native anatomies.
Figure 4:
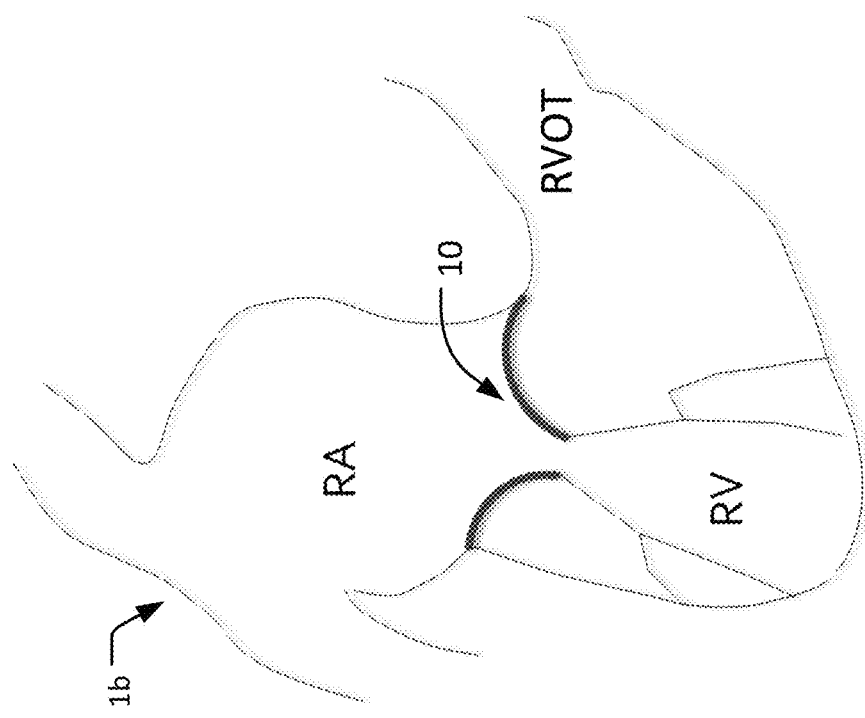
FIG. 4 shows a schematic view of the right side of the heart of FIG. 3, including the right atrium ("RA"), right ventricle ("RV"), and right ventricle outflow tract ("RVOT"), in accordance with some native anatomies.

FIGS. 4 and 5 schematically illustrate the right side of the heart 1, including the right atrium, right ventricle, and tricuspid valve 10 therebetween. Naturally, there is anatomical variability among the human population. FIGS. 4 and 5 depict some of the anatomical variability. In particular, FIG. 4 shows a heart 1a that includes the presence of a posterior shelf 11. In contrast, FIG. 5 shows a heart 1b with a lack of any such posterior shelf. Some human hearts (such as the heart 1a) have a posterior shelf 11, but some human hearts (such as the heart 1b) do not have a distinct posterior shelf. Fortunately, the prosthetic tricuspid valves disclosed herein can be implanted in the native tricuspid valve 10 of both types of anatomies (e.g., both the heart 1a with the posterior shelf 11, and the heart 1b without the posterior shelf).

The posterior shelf 11, when present, provides an anatomical structure that can be used advantageously for the anchorage of a prosthetic tricuspid valve (as described further herein). When no such posterior shelf is present (e.g., as shown in FIG. 5), robust anchorage of a prosthetic tricuspid valve at the site of the native tricuspid valve 10 is more challenging. Nevertheless, as described further herein, the prosthetic tricuspid valves described herein can be successfully used in such a case.

Figure 6:
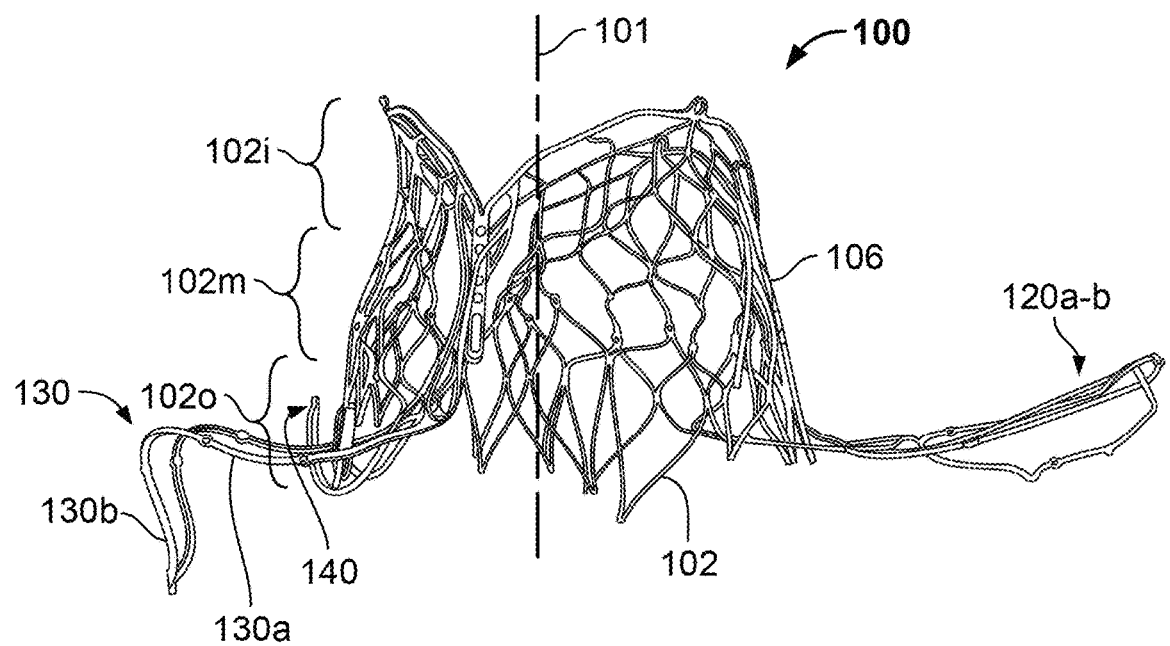
FIG. 6 shows a side view of a frame of an example prosthetic heart valve in accordance with some embodiments described herein.
Figure 7:
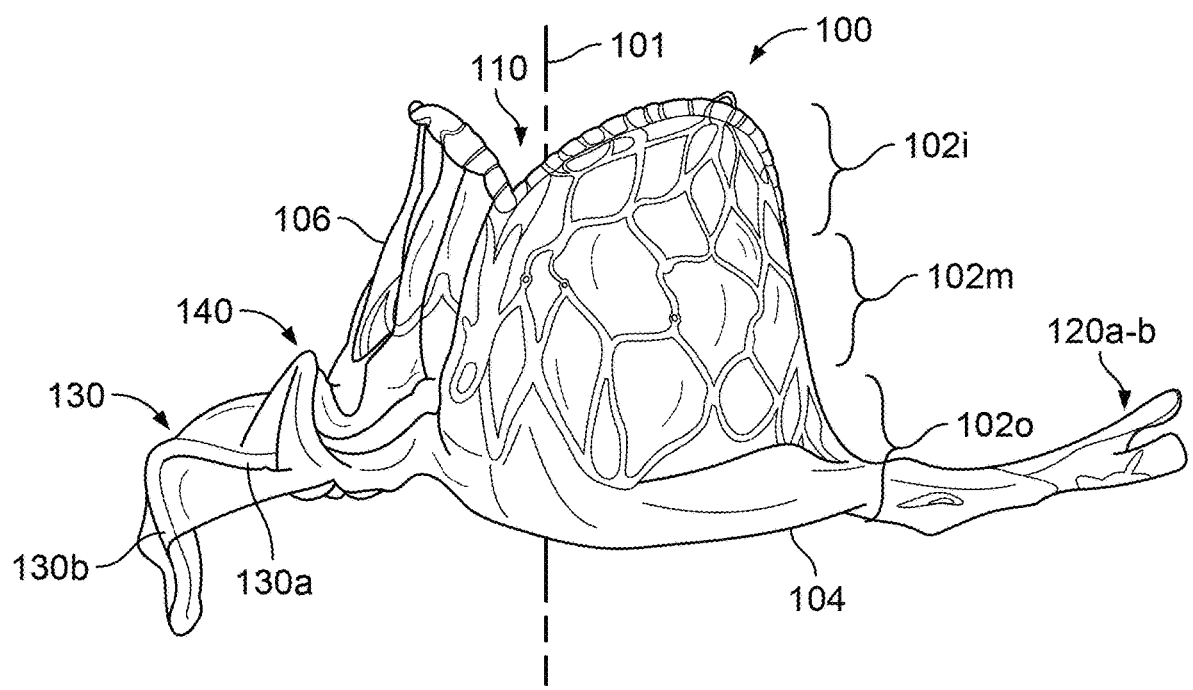
FIG. 7 shows a side view of an example prosthetic heart valve that includes the frame of FIG. 6.
Figure 8:
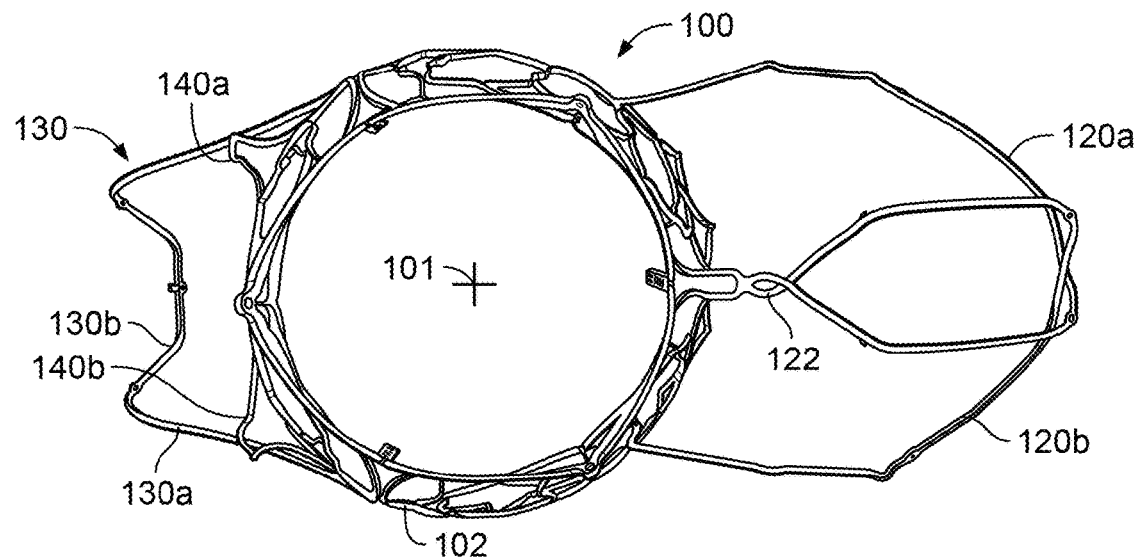
FIG. 8 shows a top view of the frame of FIG. 6.
Figure 9:
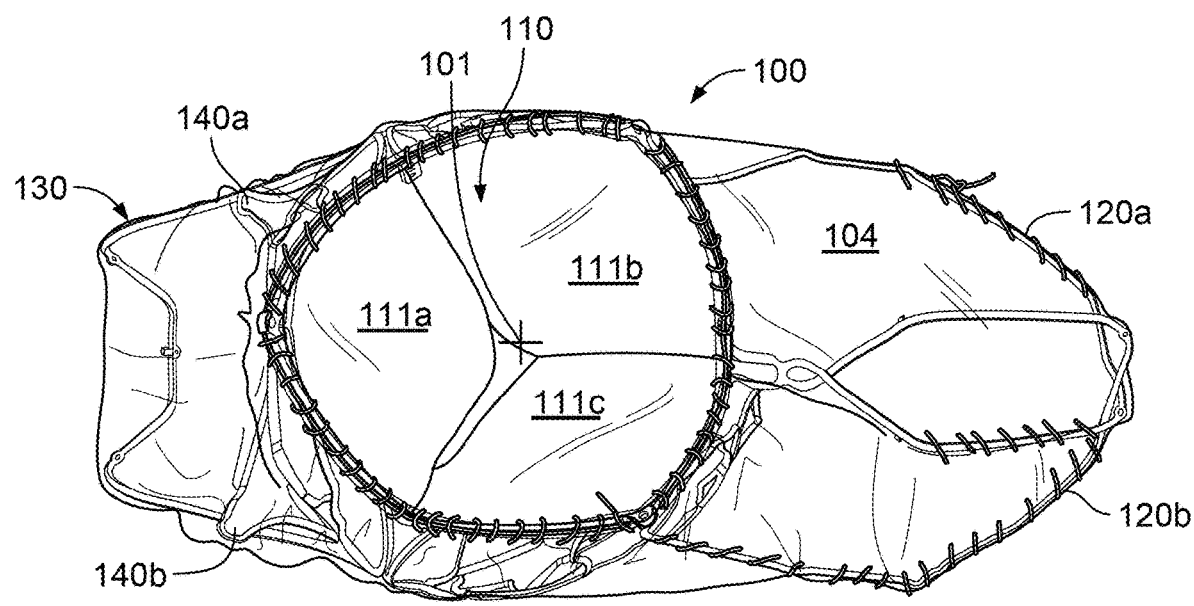
FIG. 9 shows a top view of the prosthetic heart valve of FIG. 7.

FIGS. 6-9 illustrate an example prosthetic tricuspid valve 100 (or simply "valve 100") in accordance with some example embodiments of this disclosure. The valve 100 includes a frame 102 and a covering 104 attached to the frame 102. FIGS. 6 and 8 show the frame 102 alone. FIGS. 7 and 9 show the covering 104 attached to the frame 102 (which is the full configuration of the valve 100).

The frame 102 comprises a cellular structure that provides mechanical support for the shape and structures of the valve 100. In some embodiments, the frame 102 is made from nitinol (NiTi), stainless steel, cobalt chromimum, MP35N, titanium, polymeric materials, other biocompatible materials, or any combination thereof. Some or all parts of the frame 102 may be covered by the covering 104. The frame 102 can be made of a laser cut, expanded, and shape-set material in some embodiments. In some embodiments, the precursor material is tubular NiTi, a NiTi sheet, or other suitable types of precursor materials.

The covering 104 may made of a biocompatible polymer material (e.g., expanded polytetrafluoroethylene (ePTFE), UHMWPE (ultra-high molecular weight polyethylene), nylon, polyester (e.g., DACRON), or another synthetic material), natural tissues (e.g., bovine, porcine, ovine, or equine pericardium), or any combination thereof. The covering 104 can be attached to the frame 102 by suturing, using clips, and/or any other suitable attachment process.

The valve 100 includes a main body 106. The main body 106 includes an occluder 110 that defines a central axis 101. The occluder 110 has flexible leaflets 111a, 111b, and 111c (collectively 111a-c) that cause the occluder 110 to function as a one-way valve (in a manner like a native tricuspid valve). The occluder 110 defines a circular inlet where the edges of leaflets 111a-c are attached to the frame 102. Other side edges of the leaflets 111a-c are attached to posts 112a, 112b, and 112c of the frame 102. The leaflets 111a-c also have distal free edges that are coaptable with each other to facilitate the opening and scaling of the occluder 110.

The main body 106 of the valve 100 includes an inflow end portion 102i, a mid-body portion 102m, and an outflow end portion 102o. The inflow end portion 102i includes a series of arch shapes in the frame 102, circumscribing the axis 101 of the occluder 110. The occluder leaflets 111a-c allow blood to directionally flow through the occluder 110 from the inflow end portion 102i to the outflow end portion 102o. The leaflets 111a-c of the occluder 110 close against each other (e.g., coapt) to prevent blood flow in the other direction (to prevent blood flow from the outflow end portion 102o to the inflow end portion 102i).

The embodiments of the valve 100 depicted in this disclosure employ three occluder leaflets 111a-c, which is referred to as tri-leaflet occluder. The occluder 110 of the valve 100 can optionally employ configurations other than a tri-leaflet occluder. For example, bi-leaflet, quad-leaflet, or mechanical valve constructs can be used in some embodiments. In particular implementations described herein, the flexible leaflets 111a-e are made of natural tissues such as porcine or bovine or equine or ovine pericardium. In such embodiments, the tissues are chemically cross-linked using glutaraldehyde or formaldehyde, or other aldehydes commonly used as crosslinking agents. In other embodiments, the flexible leaflets 111a-c are made of polymers such as polyurethane, polyester (DACRON) or expanded polytetrafluoroethylene (ePTFE). In some embodiments, the flexible leaflets 111a-c are attached to structural frame 102 using sutures that could be made of materials including but not limited to UHMWPE, nylon, or polyester (e.g., DACRON).

The valve 100 also includes a first anterior flap 120a, a second anterior flap 120b, and a posterior flap 130. The frame 102 and the covering 104 combine to form the anterior flaps 120a-b and the posterior flap 130. The frame 102 provides the structure of the anterior flaps 120a-b and the posterior flap 130, and the covering 104 provides occlusion. While the depicted embodiment includes two anterior flaps 120a-b, in some embodiments one, three, four, or more than four anterior flaps can be included. While the depicted embodiment includes a single posterior flap 130, in some embodiments two, three, four, or more than four posterior flaps can be included.

The anterior flaps 120a-b and the posterior flap 130 extend away from the outflow end portion 102o of the main body 106 in opposite directions away from the axis 101. That is, the posterior flap 130 extends directionally opposite from the extension direction of the first and second anterior flaps 120a-b. In some embodiments, the posterior flap 130 extends 180° opposite from the extension direction of the first and second anterior flaps 120a-b. In particular embodiments, the anterior flaps 120a-b and the posterior flap 130 extend away from the outflow end portion 102o of the main body 106 transverse to the axis 101 of the occluder 110.

In the depicted embodiment, the posterior flap 130 includes a first portion 130a and a second portion 130b that are arranged at an angle in relation to each other. The first portion 130a extends away from the outflow end portion 102o of the main body 106 generally transverse to the axis 101 of the occluder 110. The second portion 130b of the posterior flap 130 extends from the first portion 130a. In the depicted embodiment, the second portion 130b extends generally parallel to the axis 101 of the occluder 110. The angle defined between the first portion 130a and the second portion 130b can be in a range of 80° to 100°, or 70° to 110°, or 60° to 120°, or 50° to 130°, or 40° to 140°, without limitation.

The first anterior flap 120a and the second anterior flap 120b each extend in the same direction, which is opposite of the direction that the posterior flap 130 extends. In the depicted embodiment, portions of the first anterior flap 120a and the second anterior flap 120b overlap each other. An advantage of having the two separate anterior flaps 120a-b (rather than a single larger anterior flap) is that the anterior flap portion of the valve 100 can be radially compressed to a smaller profile for transcatheter delivery by the virtue of having the two separate anterior flaps 120a-b (as compared to having a single larger anterior flap).

In some embodiments, the first and second anterior flaps 120a-b extend into the RVOT and overlap one axially on top of the other. This arrangement is functionally akin to a cantilevered beam arrangement. With the first and second anterior flaps 120a-b overlapping on each other, the bending resistance of the first and second anterior flaps 120a-b is increased (as compared to a single flap or non-overlapping flaps). This arrangement enables an advantageous extent of rigidity, without having to use framework members that are larger in cross-section. That is, the overlapping arrangement of the first and second anterior flaps 120a-b allow for the use of smaller framework members, which in turn importantly allows for a smaller collapsed delivery size (diameter). In other words, overlapping arrangement of the first and second anterior flaps 120a-b provides a support structure that is thicker without having to use a material with higher wall thickness (from which the framework is created); ultimately providing the bending stiffness or rigidity that keeps the valve 100 stable when RV pressure acts on the valve 100.

Figure 38:
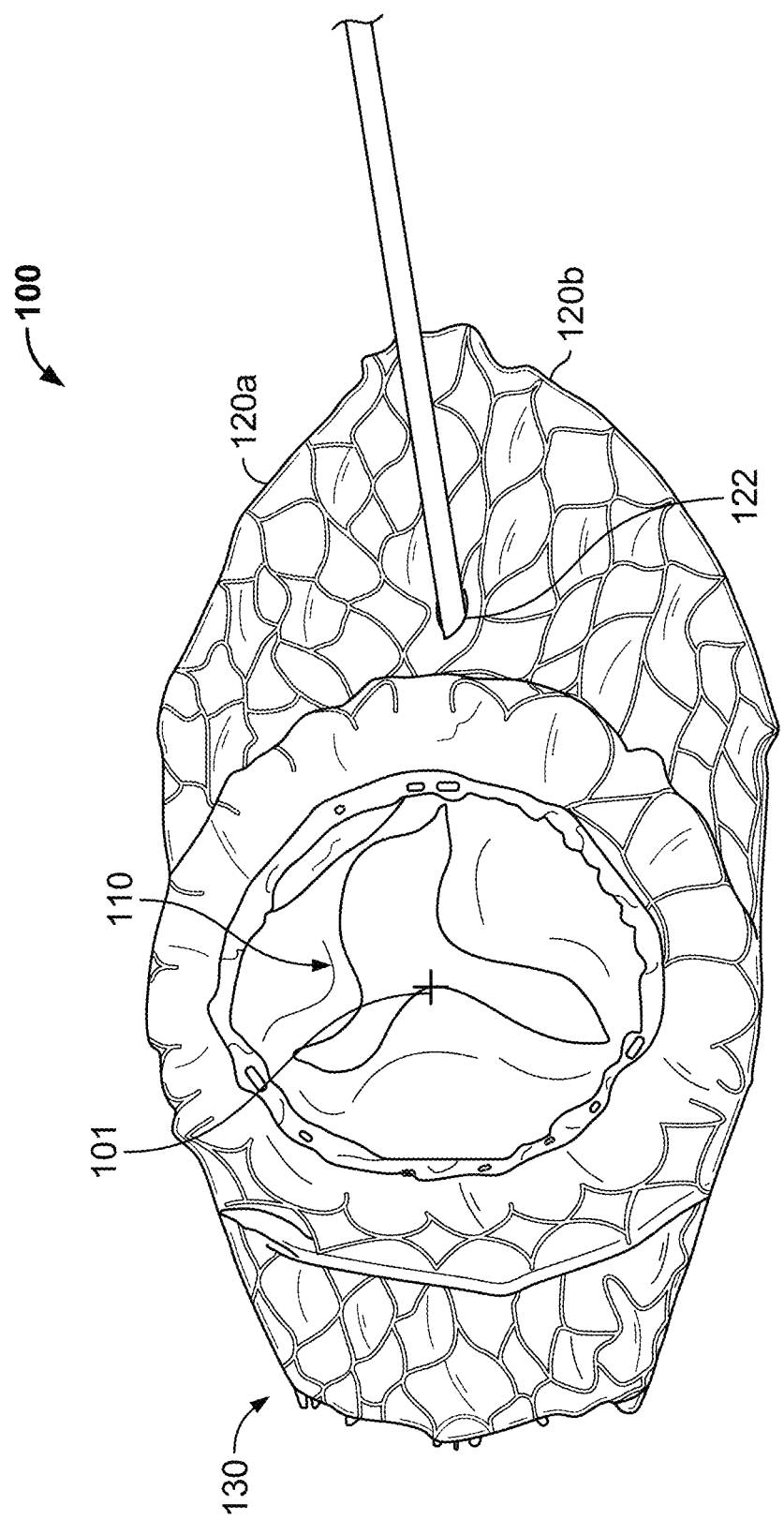
FIG. 38 is a top view of another example prosthetic heart valve in accordance with some embodiments, and illustrates a pacemaker lead extending through an opening defined between the two anterior flaps of the prosthetic heart valve.

In the depicted embodiment, an open passage 122 (e.g., see FIG. 8) is defined between the first anterior flap 120a and the second anterior flap 120b. This is also shown in FIG. 38. The open passage 122 can be used, for example, for passing a pacemaker lead through the valve 100, without disturbing the functioning of the occluder 110. Accordingly, the valve 100 can facilitate the pass-through of the pacemaker lead while still providing sealing to prevent tricuspid valve regurgitation from the RV to the RA. In some cases, the pacemaker lead is pre-existing and the valve 100 is implanted subsequently (with the open passage 122 being used to receive the pacemaker lead). In other cases, the valve 100 can be pre-existing and the pacemaker lead can be subsequently passed through the open passage 122.

The valve 100 also includes one or more leaflet engagement members 140. In the depicted embodiment, the valve 100 includes two leaflet engagement members: a first leaflet engagement member 140a and a second engagement member 140b. In the depicted embodiment, the leaflet engagement members 140a-b extend from the outflow end portion 102o of the main body 106. In some embodiments, the leaflet engagement members 140a-b extend from the mid-body portion 102m of the main body 106.

The leaflet engagement members 140a-b extend from the frame 102 and bend toward the inflow end portion 102i of the main body 106. In other words, a portion of each leaflet engagement member 140a-b extends toward the inflow end portion 102i of the main body 106. A space, groove, or slot is defined between the leaflet engagement members 140a-b and the outer surface of the frame 102 (with the covering 104 being present on the frame 102 and leaflet engagement members 140a-b). As described further below, the space, groove, or slot receives and mechanically captures/holds a portion of a native leaflet to provide migration resistance for the valve 100.

In the depicted embodiment, the leaflet engagement members 140a-b extend from the frame 102 of the main body 106 in the same direction as the posterior flap 130. The posterior flap 130 extends away from the main body 106 farther than the leaflet engagement members 140a-b. As described further below, various other arrangements of the leaflet engagement members 140a-b and the posterior flap 130 are also envisioned and within the scope of this disclosure.

The leaflet engagement members 140a-b may be U-shaped wire loops, as in the depicted embodiment. The wire loops that make up the leaflet engagement members 140a-b can be continuous with the wire members of the frame 102.

In the depicted embodiment, the leaflet engagement members 140a-b terminate at free ends. Accordingly, the leaflet engagement members 140a-b point toward the inflow end portion 102i of the main body 106, with the free ends of the leaflet engagement members 140a-b being the closest to the inflow end portion 102i. This arrangement defines the space, groove, or slot receives and mechanically captures/holds a portion of a native leaflet to provide migration resistance for the valve 100.

Figure 10:
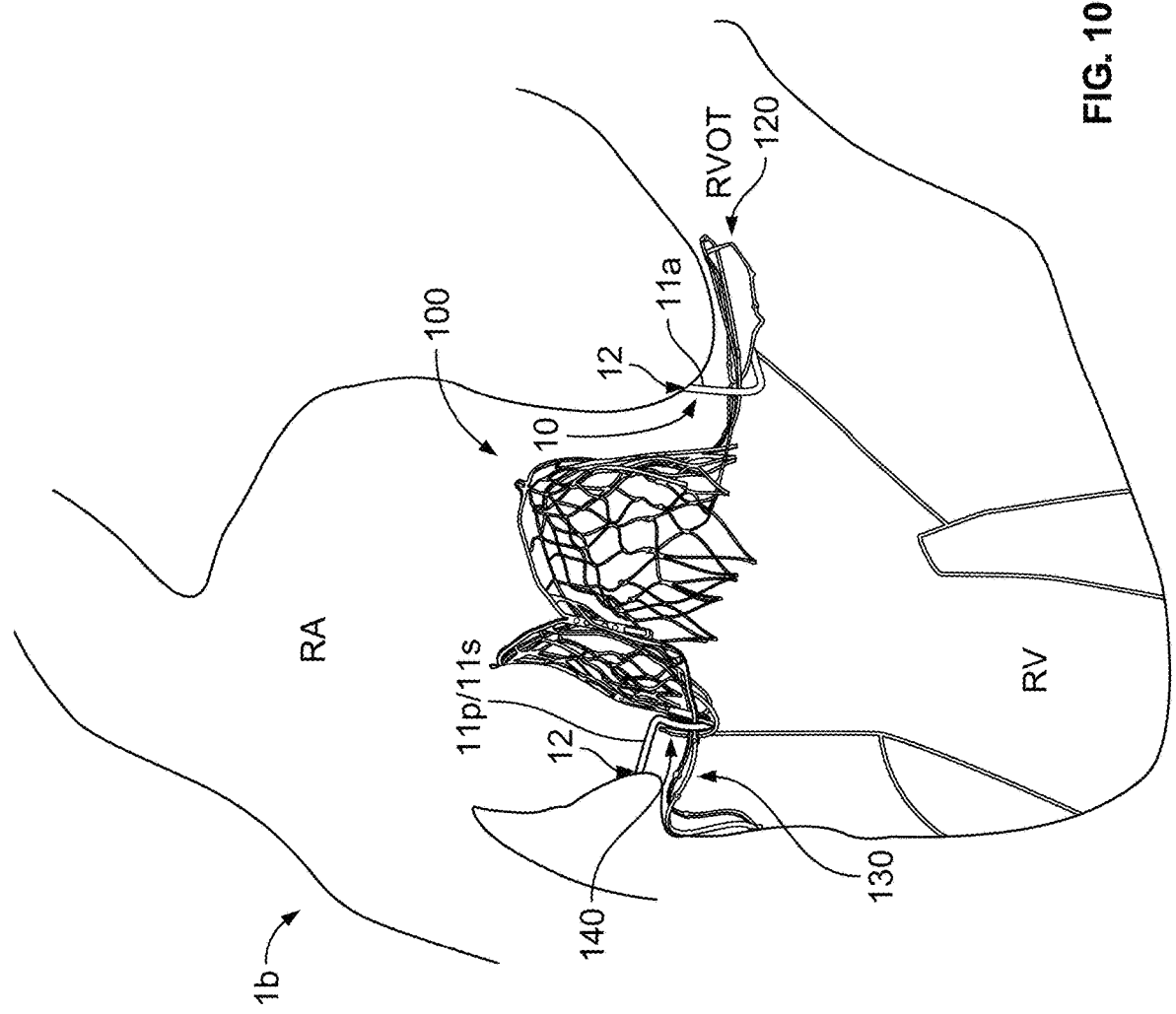
FIG. 10 schematically shows the frame of FIG. 6 positioned in an example native tricuspid heart valve location.

FIG. 10 depicts the valve 100 implanted in the heart 1b. As per FIG. 5, the heart 1b does not always naturally include a distinct posterior shelf in the right ventricle ("RV") below the annulus 12 of the native tricuspid valve 10. However, as described further below, the valve 100 is structured to induce an anchoring location that resembles a posterior shelf once the valve 100 is fully deployed. The valve 100 is shown here without the covering 104 to provide additional clarity of the orientation of the valve 100 relative to the native tricuspid valve 10 and the other structures of the heart 1b.

In FIG. 10, it can be seen that the posterior leaflet 11p and/or the septal leaflet 11s is captured and held by the leaflet engagement member(s) 140. This provides anchorage and migration resistance of the valve 100. Additionally, the posterior flap 130 of the valve 100 atraumatically presses against the wall of the RV just below the annulus 12 of the native tricuspid valve 10. In that manner, the posterior flap 130 nestles against the wall of the RV just below the annulus 12 and provides additional anchorage and migration resistance of the valve 100. Further, the anterior flap(s) 120 provide anchorage for the valve 100 by opposing against the wall of the RV below the anterior leaflet 11a of the tricuspid valve 12, and by opposing against the wall that defines the inlet to the RVOT. For example, during contraction of the RV, the anterior flap(s) 120 become pressed against the wall of the RVOT to help prevent the valve 100 from being pushed into the RA because of the pressure differential between the RV and RA during contraction of the RV.

Figure 12:
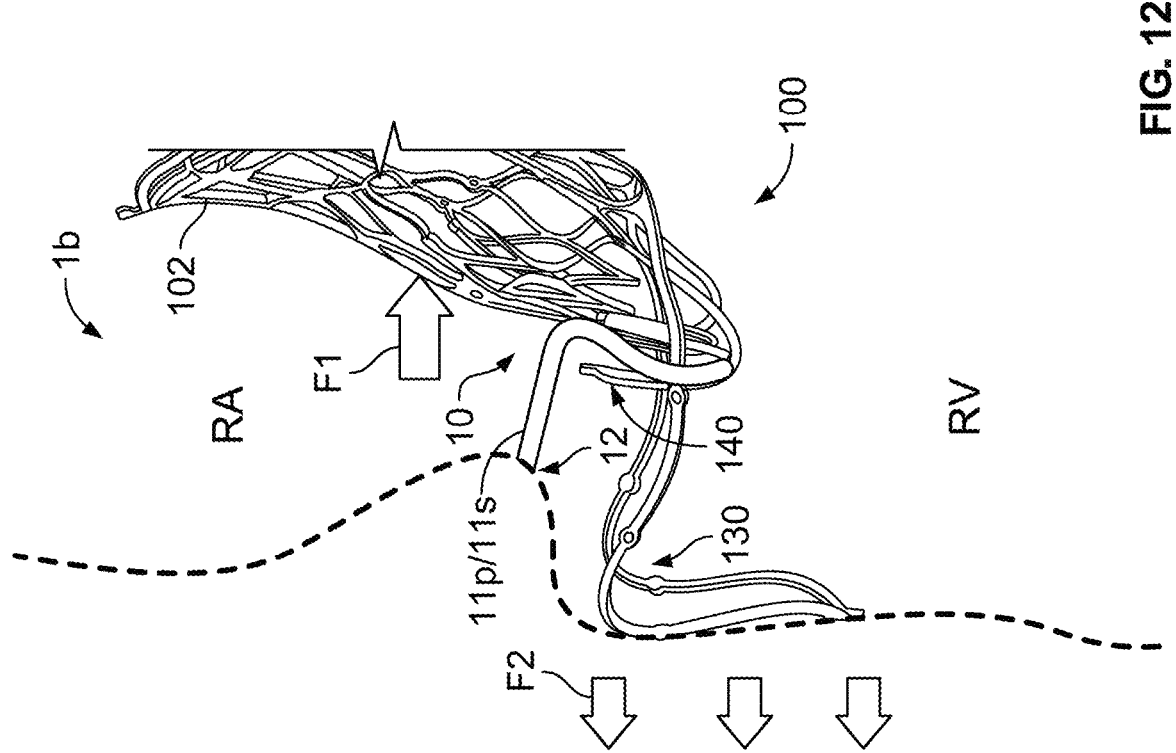
FIG. 12 schematically shows a portion of the frame of FIG. 6 positioned in the example anatomy of FIG. 11.
Figure 11:
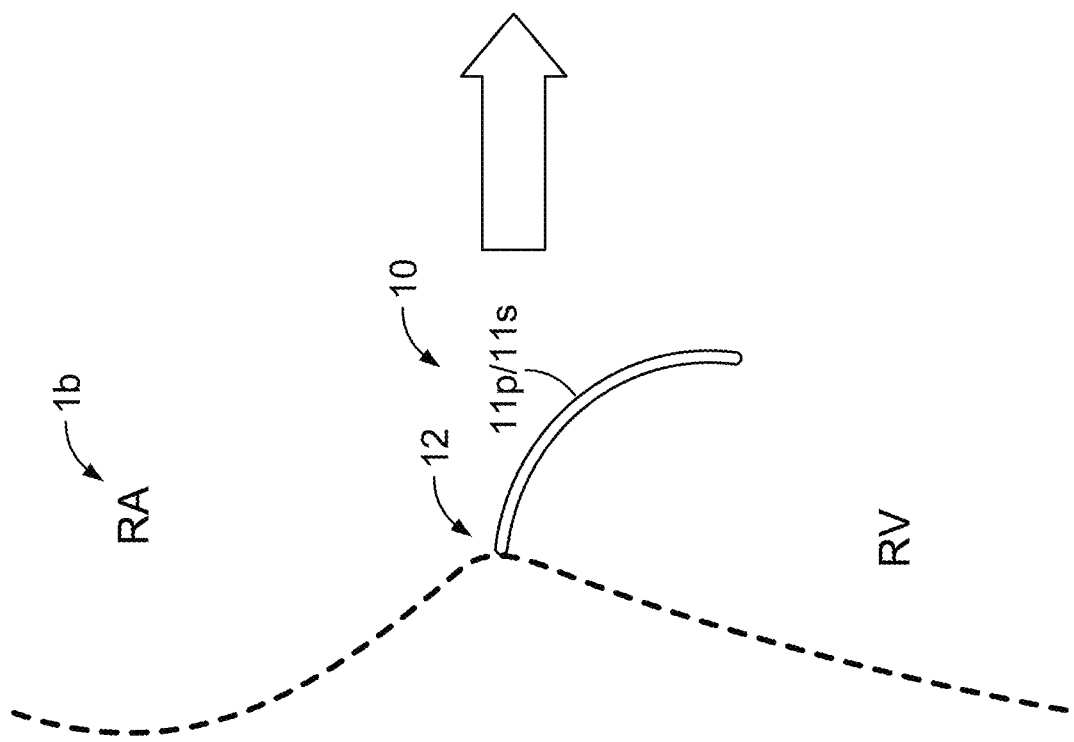
FIG. 11 schematically shows a posterior leaflet of a native tricuspid valve and the walls of a right atrium and right ventricle in accordance with some native anatomies.

FIGS. 11 and 12 provide the bases for additional information regarding how the valve 100 can provide robust anchorage and migration resistance even in the case of the anatomy of the heart 1b that, from a natural standpoint, exhibits no distinct posterior shelf (e.g., as compared to the heart 1a of FIG. 4). In FIG. 12, the valve 100 is implanted in the tricuspid valve 10 of the heart 1b.

As illustrated in FIG. 12, the valve 100 anchors in relation to the posterior region of the native tricuspid valve 10 using opposing forces. That is, a first force F1 (as indicated by the arrow F1) results because the posterior leaflet 11p and/or the septal leaflet 11s captured and held by the leaflet engagement member(s) 140. Additionally, a second force F2 (as indicated by the arrows F2) results because the posterior flap bears against the wall of the RV beneath the annulus 12 of the tricuspid valve 10. The forces F1 and F2 act in opposite directions of each other. It can be said that force F1 pulls on the posterior leaflet 11p and/or the septal leaflet 11s and force F2 pushes on the wall of the RV. This push-pull arrangement of opposing forces results in a secure anchorage and robust migration resistance of the valve 100 relative to the native tricuspid valve 10.

Figure 13:
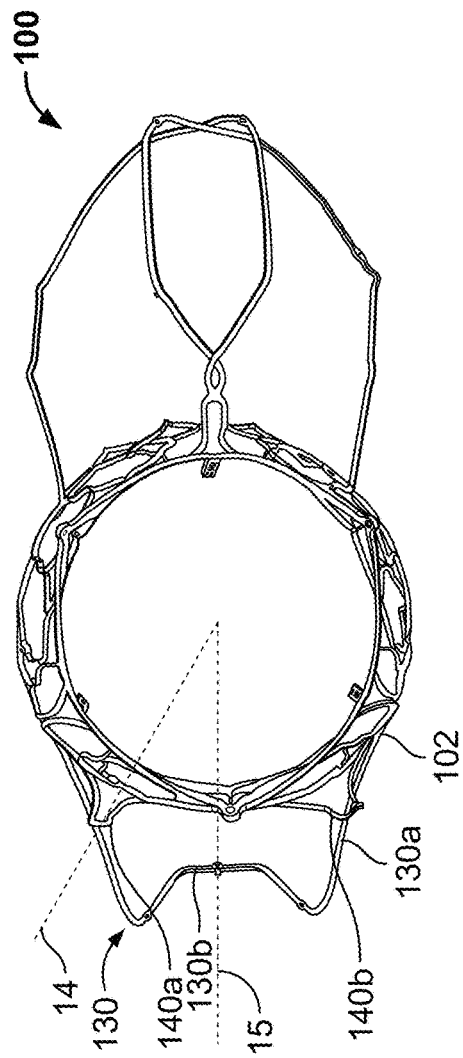
FIG. 13 shows a top view of the frame of FIG. 6 and two cut-planes through the frame.

FIG. 13 is another top view of the frame 102 of the valve 100. Two cut-planes are indicated by the dashed lines. The first cut-plane 14 corresponds to the view of FIG. 14. This view passes through the first leaflet engagement member 140a. The second cut-plane 15 corresponds to the view of FIG. 15. This view is along the frame 102 between the leaflet engagement members 140a and 140b.

Figure 14:
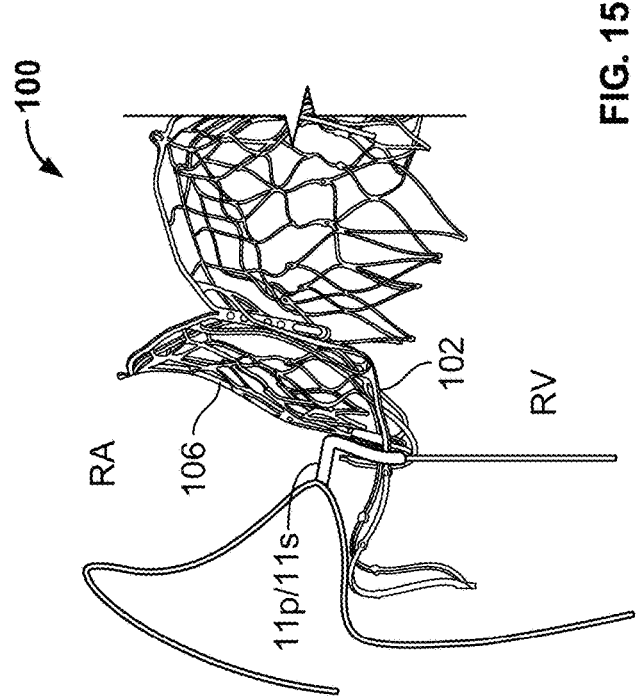
FIG. 14 schematically shows a cross-sectional portion of the frame of FIG. 13, taken along a first cut-plane of FIG. 13, and positioned in the example anatomy of FIG. 11.

As shown in FIG. 14, the posterior leaflet 11p and/or the septal leaflet 11s captured and held by the first leaflet engagement member 140a. That is, the posterior leaflet 11p and/or the septal leaflet 11s is held captive within the space between the first leaflet engagement member 140a and the main body 106. While it is not visible in this view, the same is true about the second leaflet engagement member 140b. That is, the posterior leaflet 11p and/or the septal leaflet 11s is held captive within the space between the second leaflet engagement member 140b and the main body 106.

Figure 15:
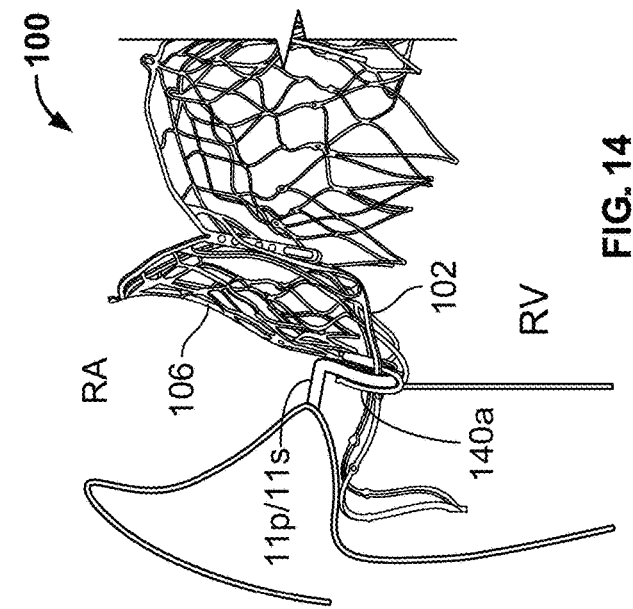
FIG. 15 schematically shows a cross-sectional portion of the frame of FIG. 13, taken along a second cut-plane of FIG. 13, and positioned in the example anatomy of FIG. 11.
Figure 33:
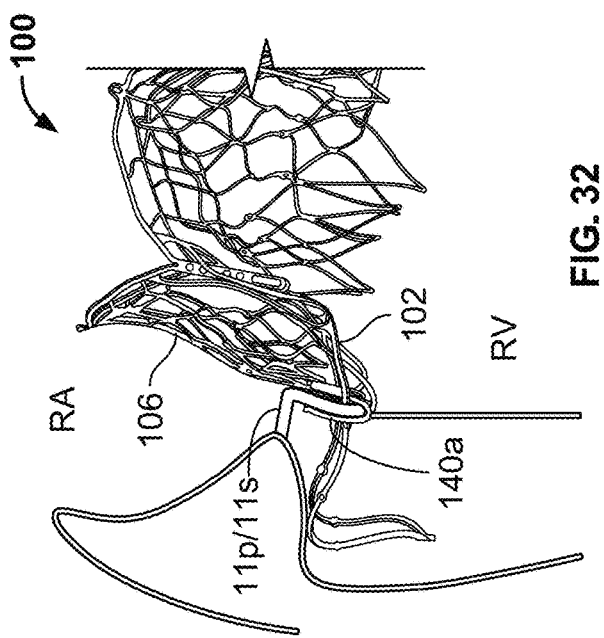
FIG. 33 schematically shows a cross-sectional portion of the frame of FIG. 31, taken along a second cut-plane of FIG. 31, and positioned in the example anatomy of FIG. 29.

As shown in FIG. 15, in the depicted example implementation the posterior leaflet 11p and/or the septal leaflet 11s is abutting the frame 102 along the portion of the main body 106 that extends between the leaflet engagement members 140a and 140b. Of course, in reality the valve 100 includes a covering 104 on the frame 102. Therefore, the posterior leaflet 11p and/or the septal leaflet 11s would be actually abutting the covering 104 that is on the frame 102. The arrangement depicted in FIG. 15 occurs in some cases. In other cases (such as depicted in FIG. 33), portions of the posterior leaflet 11p and/or the septal leaflet 11s between the leaflet engagement members 140a and 140b do not reside so closely to the frame 102 as is depicted in FIG. 15.

FIGS. 16-23 schematically illustrate four different variations of the valve 100. The differences between the four different variations concern the arrangement of the posterior flap 130 and the leaflet engagement member(s) 140. Otherwise, in general, the four different variations of the valve 100 (referred to as valve 100a, valve 100b, valve 100c, and valve 100d) share the features of the valve 100 as described herein.

Figure 16:
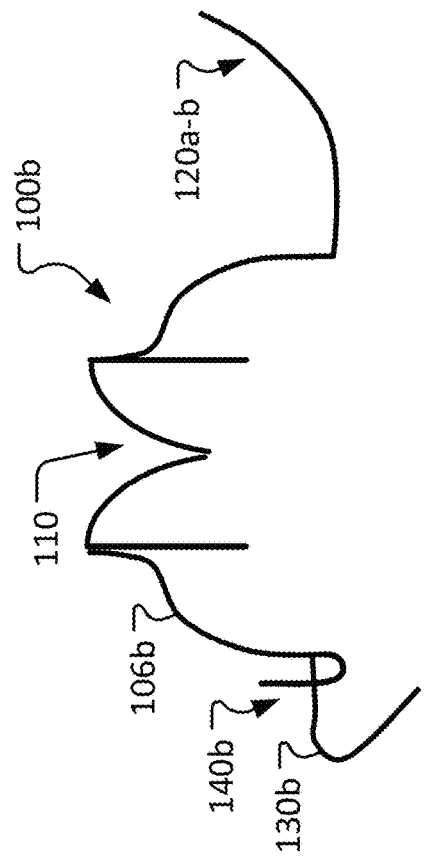
FIG. 16 schematically shows a side view of an example prosthetic tricuspid valve in accordance with some embodiments.
Figure 17:
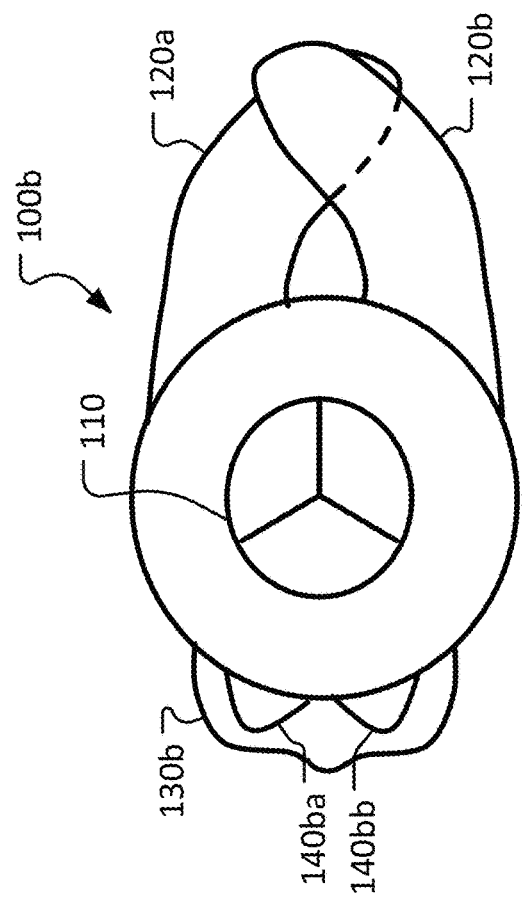
FIG. 17 shows a side view of the example prosthetic tricuspid valve of FIG. 16.

FIGS. 16 and 17 illustrate an example valve 100a. The valve 100a includes the main body 106a (and covering 104), the occluder 110, the anterior flaps 120a-b, the posterior flap 130a, the first leaflet engagement member 140aa and the second engagement member 140ab. From the top view of FIG. 17, it can be seen that the posterior flap 130a extends away from the main body 106a between the first leaflet engagement member 140aa and the second engagement member 140ab. The first leaflet engagement member 140aa is located on one side of the posterior flap 130a, and the second engagement member 140ab is located on the other side of the posterior flap 130a.

Figure 18:
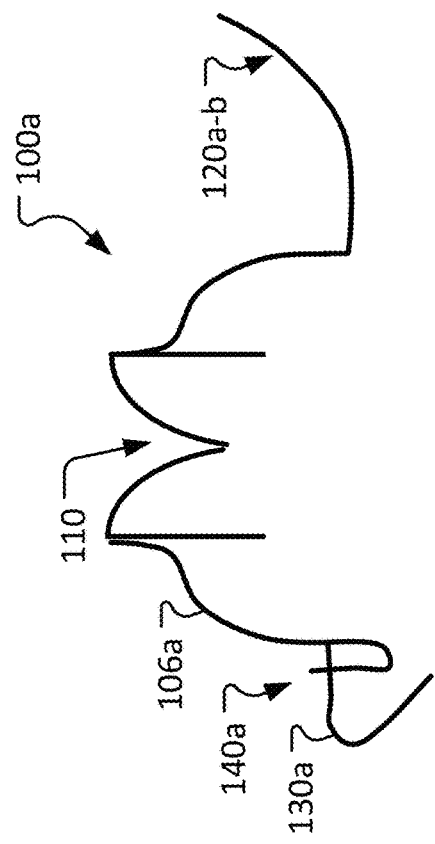
FIG. 18 schematically shows a side view of another example prosthetic tricuspid valve in accordance with some embodiments.
Figure 19:
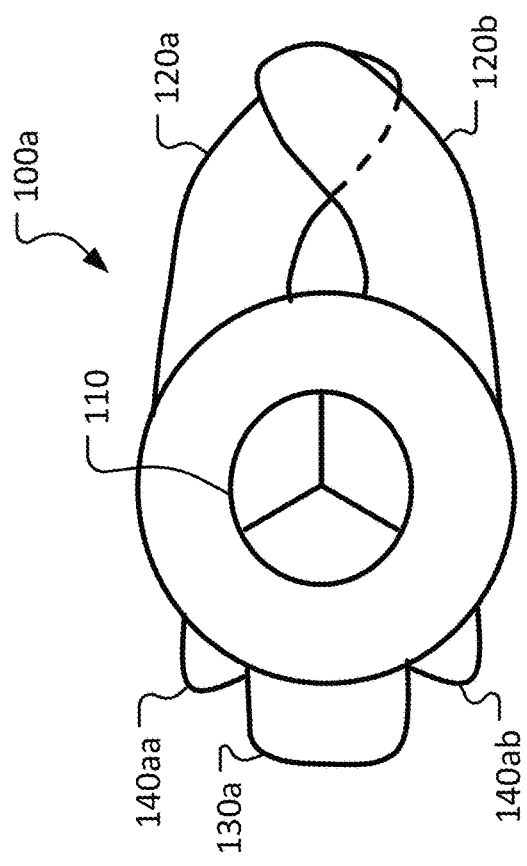
FIG. 19 shows a side view of the example prosthetic tricuspid valve of FIG. 18.

FIGS. 18 and 19 illustrate an example valve 100b. The valve 100b includes the main body 106b (and covering 104), the occluder 110, the anterior flaps 120a-b, the posterior flap 130b, the first leaflet engagement member 140ba and the second engagement member 140bb. From the top view of FIG. 19, it can be seen that the first leaflet engagement member 140ba and the second engagement member 140bb extend away from the main body 106b within the outer periphery of the posterior flap 130b. As shown in FIG. 19, the posterior flap 130b is wider than the combined widths of the first leaflet engagement member 140ba and the second engagement member 140bb.

Figure 20:
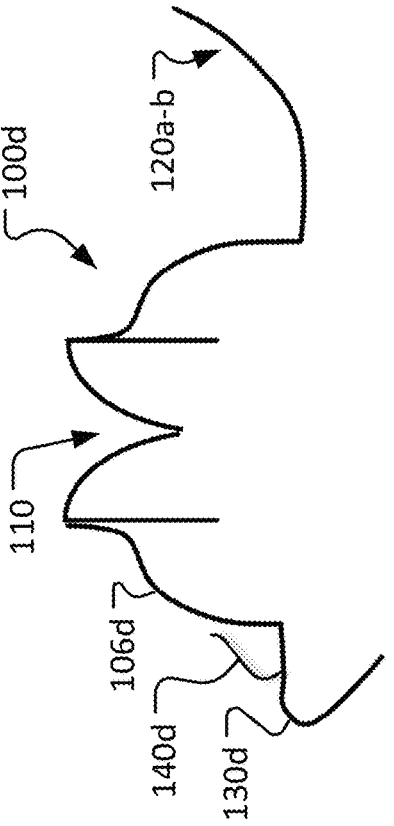
FIG. 20 schematically shows a side view of another example prosthetic tricuspid valve in accordance with some embodiments.
Figure 21:
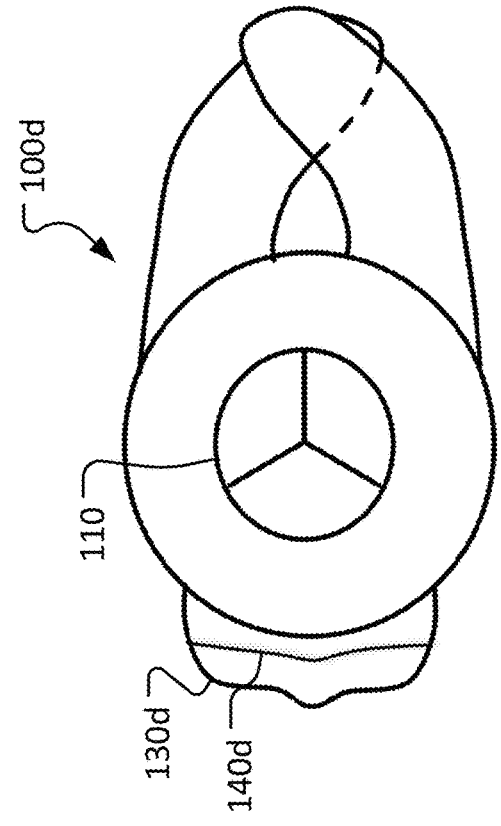
FIG. 21 shows a side view of the example prosthetic tricuspid valve of FIG. 20.

FIGS. 20 and 21 illustrate an example valve 100c. The valve 100c includes the main body 106c (and covering 104), the occluder 110, the anterior flaps 120a-b, the posterior flap 130c, and a single leaflet engagement member 140c. From the top view of FIG. 21, it can be seen that the single leaflet engagement member 140c extends away from the main body 106c within the outer periphery of the posterior flap 130c. The posterior flap 130c is more than twice of the width of the single leaflet engagement member 140c. The single leaflet engagement member 140c is centered in relation to the posterior flap 130c. In other embodiments, the single leaflet engagement member 140c is not centered in relation to the posterior flap 130c.

Figure 22:
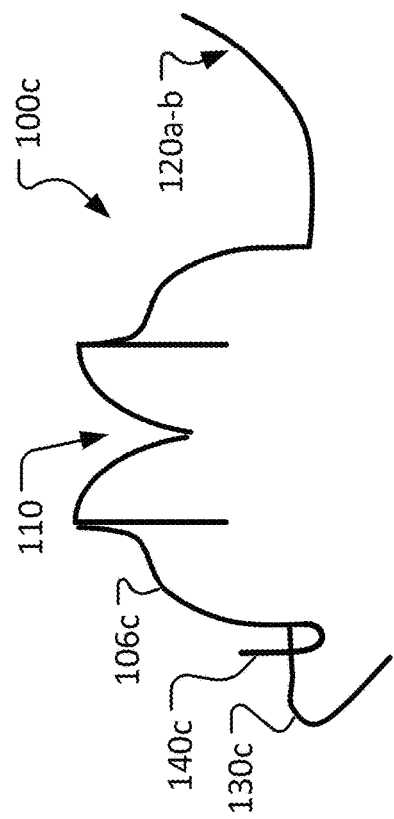
FIG. 22 schematically shows a side view of another example prosthetic tricuspid valve in accordance with some embodiments.
Figure 23:
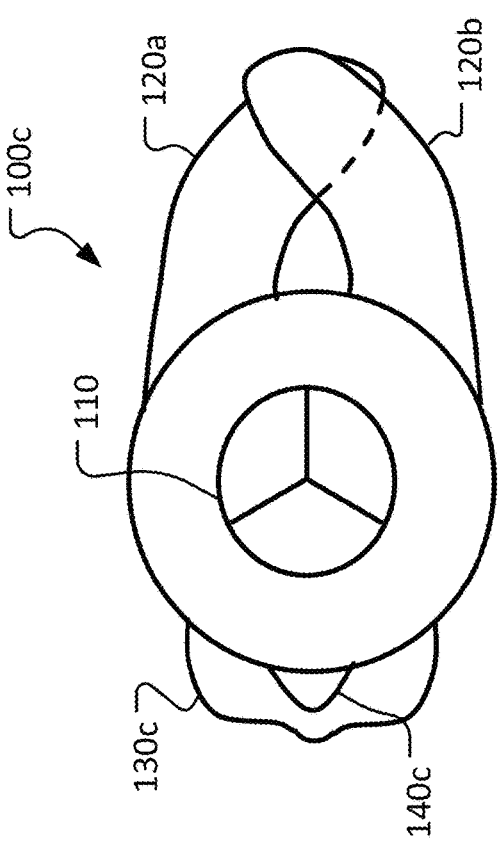
FIG. 23 shows a side view of the example prosthetic tricuspid valve of FIG. 22.

FIGS. 22 and 23 illustrate an example valve 100d. The valve 100d includes the main body 102d (and covering 104), the occluder 110, the anterior flaps 120a-b, the posterior flap 130d, and a single leaflet engagement member 140d. From the top view of FIG. 23, it can be seen that the single leaflet engagement member 140d extends along an entire width of the posterior flap 130d (from one edge of the posterior flap 130d to an opposite edge of the posterior flap 130d). The single leaflet engagement member 140d extends from the posterior flap 130d (rather than extending from the main body 106d). In other embodiments, the single leaflet engagement member 140d extends from the main body 106d.

FIGS. 24-28 are a series of schematic illustrations that depict the major steps of a deployment process of the valve 100. The valve 100 is deployable using a transcatheter technique. While the deployment of the valve 100 is described in these figures in the context of a tricuspid valve replacement, the valve 100 can also be used for mitral, aortic and pulmonary valves replacements. Similar steps to deploy the valve 100 can be followed for the mitral, aortic and pulmonary valves.

As shown in FIG. 24, the valve 100 is initially contained within a delivery sheath catheter 200, and is around an inner catheter 210. The sheath catheter 200 and/or the inner catheter 210 can be steerable or deflectable in some embodiments. In some embodiments, the inner catheter 210 can be advanced over a guidewire.

The valve 100 is radially compressed to a low-profile delivery configuration while within the sheath catheter 200. In some embodiments, the valve 100 (or portions thereof are wrapped or folded around the inner catheter 210. For example, in some embodiments the anterior flaps 120a-b are wrapped around the inner catheter 210. The valve 100 can self-expand as emergence from the sheath catheter 200 (or relief from other types of containment as described below) takes place.

In some embodiments, when the valve 100 is in its collapsed delivery configuration within the delivery sheath catheter 200, the portions of the valve 100 are arranged relative to each other as follows. The first and second anterior flaps 120a-b (which can be wrapped on each other) are distal-most. The occluder portion (or valve core) with the flexible leaflets is proximal-most within the delivery sheath catheter 200. The leaflet engager(s) 140 and the posterior anchoring flap 130 are arranged between the distal-most first and second anterior flaps 120a-b and the proximal-most occluder portion.

In some embodiments, the system shown in FIG. 24 is advanced toward the patient's right atrium via either trans-jugular vein access or trans-femoral vein access. While a trans-jugular vein approach will access the right atrium through the superior vena cava, a trans-femoral vein approach will access the right atrium through the inferior vena cava. In the arrangement of FIG. 24, the outer deflectable sheath catheter 200 may be advanced and deflected to point the system towards the tricuspid annular plane.

In FIG. 25, the leaflet engagement member(s) 140 is/are released from containment within the sheath catheter 200. This can be achieved by either advancing the inner catheter 210 while holding the sheath catheter 200 stationary, or by pulling the sheath catheter 200 proximally while holding the inner catheter 210 stationary.

The leaflet engagement member(s) 140 tend to reconfigure to a natural shape or configuration when released from containment. That is, when released from containment, the leaflet engagement member(s) 140 reconfigure so that an end portion of the leaflet engagement member(s) 140 extends proximally toward the inflow end of the valve 100. As the reconfiguring of the leaflet engagement member(s) 140 takes place (to arrive at the shape shown in FIG. 25), the posterior leaflet 11p and/or the septal leaflet 11s is captured by the leaflet engagement member(s) 140. The captured portion of the posterior leaflet 11p and/or the septal leaflet 11s is held captive within the groove or space defined by the leaflet engagement member(s) 140. Capturing of the leaflet within the leaflet engagement member(s) 140 may be further facilitated by manipulations of the entire delivery system relative to the valve annulus and native leaflets, and also guided by imaging such as ultrasound, fluoroscopy, CT scanning, MRI or other imaging modalities.

In FIG. 26, the posterior flap 130 has been released from radial containment. In the depicted embodiment, the release of the posterior flap 130 is achieved by distally advancing the inner catheter 210. When that is performed, a radial containment member 211 attached to the inner catheter 210 is disengaged from the posterior flap 130. This allows the posterior flap 130 to reconfigure to a natural shape or configuration when released from containment. The deployed posterior flap 130 will become positioned in the posterior shelf area, or will abut against a wall of the right ventricle to form a pseudo posterior shelf (if the heart does not naturally have a posterior shelf).

Figure 27:
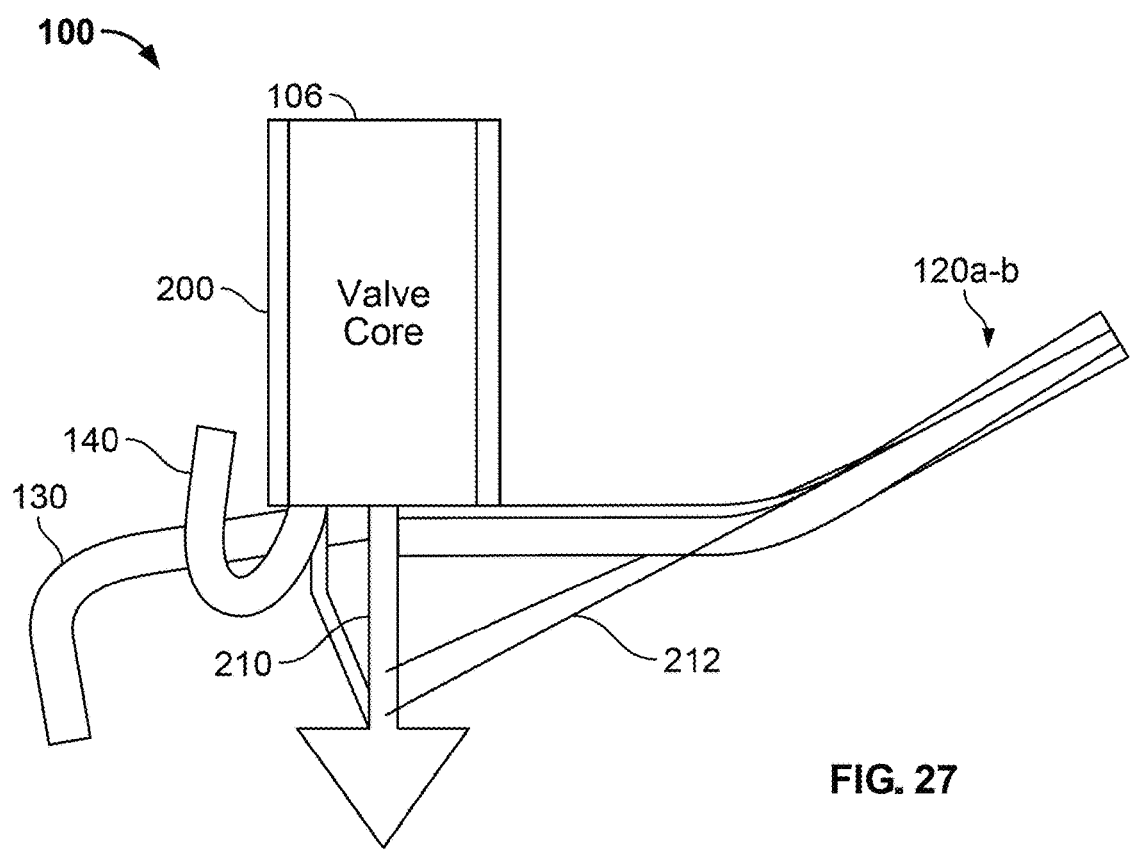
FIG. 27 schematically shows a third stage of deployment of the prosthetic heart valve from the delivery sheath of FIG. 24.

In FIG. 27, the anterior flaps 120a-b are allowed to expand radially outward toward their natural shape. This can be achieved by loosening a control wire 212 that extends from the inner catheter 210 to the anterior flaps 120a-b. In some embodiments, the inner catheter 210 can also be withdrawn proximally in order to allow the anterior flaps 120a-b to extend toward their natural shape. In some embodiments, there are two control wires 212. Each one of the anterior flaps 120a-b can have its own control wire 212. In such a case, each one of the anterior flaps 120a-b can be deployed separately from each other.

Figure 28:
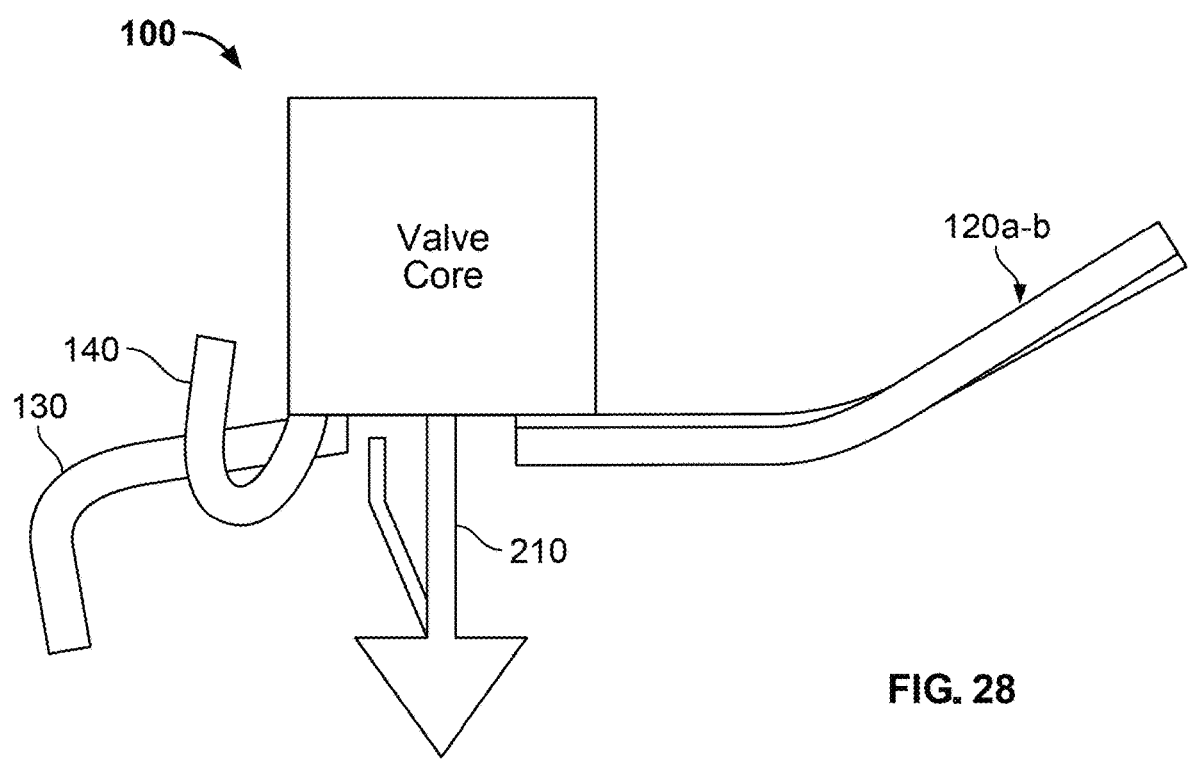
FIG. 28 schematically shows the prosthetic heart valve of FIG. 24 in a fully deployed arrangement.

In FIG. 28, the main body of the valve 100 is unsheathed, or released from its containment within the sheath catheter 200. The sheath catheter 200 can be pulled proximally off the valve 100 to accomplish this. When the unsheathing happens, the main body of the valve 100 radially expands to its fully deployed size within the annulus of the tricuspid valve. The sheath catheter 200 and the inner catheter 210 can then be removed, leaving the valve 100 to function in place of the native tricuspid valve. The frame 102 with its covering 104 acts as a sealing skirt. In addition, as described further below, the anterior flaps 120a-b also provide sealing (in addition to anchoring in the RVOT). In some embodiments, portions of the prosthetic valve 100 include an outer external anchoring skirt that extends beyond the occluder portion by 0.1 mm to 25 mm or preferably by 0.1 mm to 10 mm.

Figure 30:
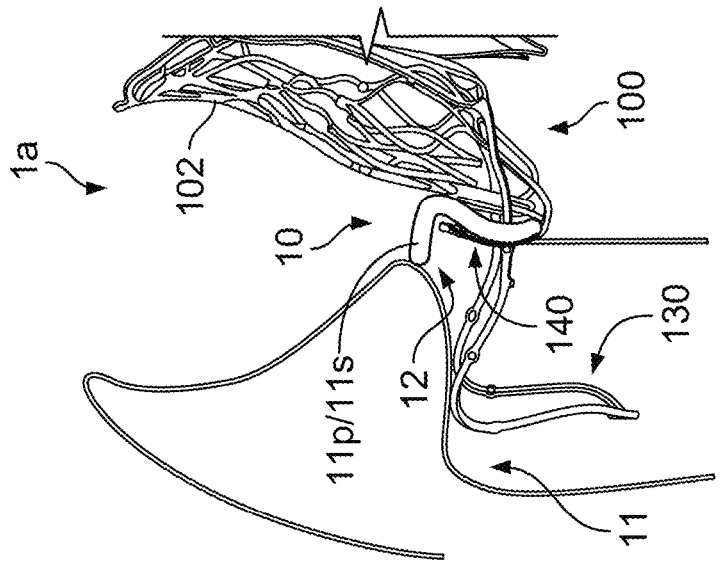
FIG. 30 schematically shows a portion of the frame of FIG. 6 positioned in the example anatomy of FIG. 29.
Figure 29:
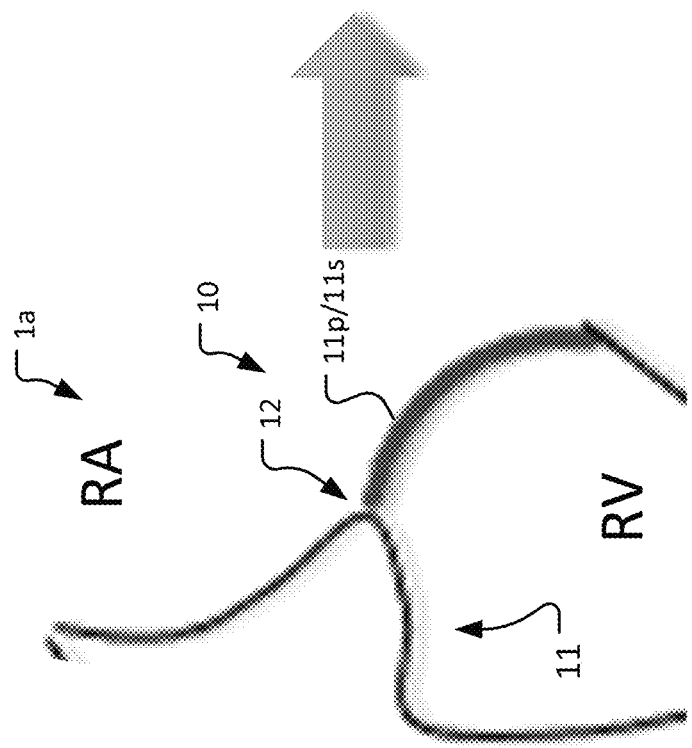
FIG. 29 schematically shows a posterior leaflet of a native tricuspid valve and the walls of a right atrium and right ventricle in accordance with some native anatomies.

FIG. 29 shows a portion of the heart 1a that naturally includes the posterior shelf 11 (see also FIG. 4). In such a case, as shown in FIG. 30, the posterior flap 130 of the valve 100 extends into the area of the posterior shelf 11 and abuts the wall of the RV just below the annulus 12 of the tricuspid valve 10. In addition, the leaflet engager(s) 140 may capture and retain the posterior leaflet 11p and/or the septal leaflet 11s. The combination of the anchoring provided by the posterior flap 130 plus the potential attachment of the leaflet engager(s) 140 to the posterior leaflet 11p and/or the septal leaflet 11s provides robust migration resistance.

Figure 31:
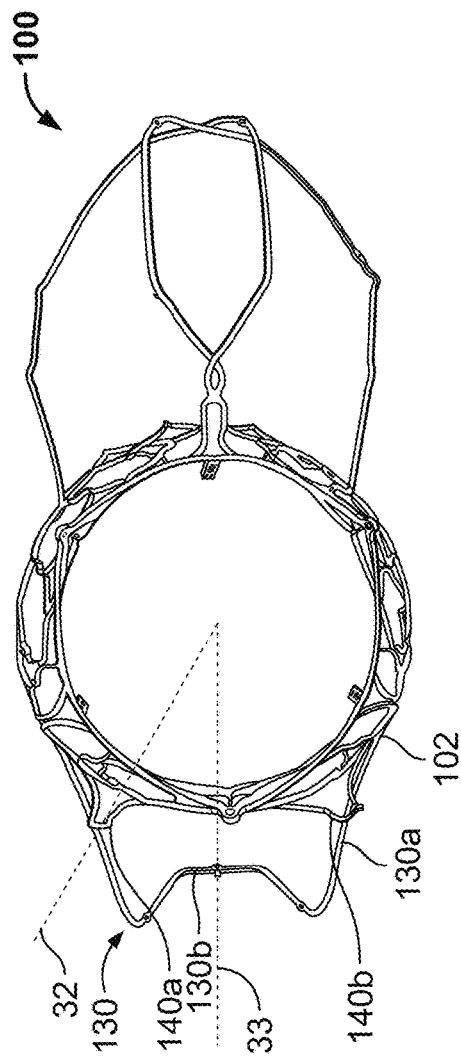
FIG. 31 shows a top view of the frame of FIG. 6 and two cut-planes through the frame.

FIG. 31 is another top view of the frame 102 of the valve 100. Two cut-planes are indicated by the dashed lines. The first cut-plane 32 corresponds to the view of FIG. 32. This view passes through the first leaflet engagement member 140a. The second cut-plane 33 corresponds to the view of FIG. 33. This view is along the frame 102 between the leaflet engagement members 140a and 140b.

Figure 32:
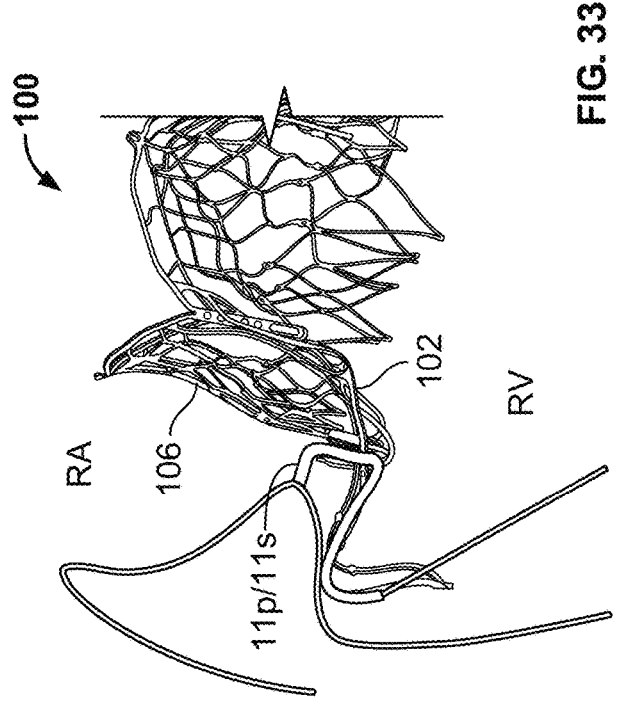
FIG. 32 schematically shows a cross-sectional portion of the frame of FIG. 31, taken along a first cut-plane of FIG. 31, and positioned in the example anatomy of FIG. 29.

As shown in FIG. 32, the posterior leaflet 11p and/or the septal leaflet 11s captured and held by the first leaflet engagement member 140a. That is, the posterior leaflet 11p and/or the septal leaflet 11s is held captive within the space between the first leaflet engagement member 140a and the main body 106. While it is not visible in this view, the same is true about the second leaflet engagement member 140b. That is, the posterior leaflet 11p and/or the septal leaflet 11s is held captive within the space between the second leaflet engagement member 140b and the main body 106.

As shown in FIG. 33, in the depicted example implementation the portion of the posterior leaflet 11p and/or the septal leaflet 11s that is between the leaflet engagement members 140a and 140b is not held captive against the main body 106. The arrangement depicted in FIG. 33 occurs in some cases. In other cases (such as depicted in FIG. 15), portions of the posterior leaflet 11p and/or the septal leaflet 11s reside closely to the main body 106.

FIGS. 34 and 35 show two side views of another example embodiment of the valve 100. The valve 100 includes a main body 106 within which the occluder 110 resides. The occluder 110 defines the central longitudinal axis 101.

In the depicted embodiment, the first anterior flap 120a and the second anterior flap 120b each include a mid-body portion 124 that is bent at an angle so as to direct terminal end portions of the anterior flaps 120a-b toward the inlet end of the main body 106. In some embodiments, the anterior flaps 120a-b initially extend away from the main body 106 substantially perpendicularly (e.g., within 80° to) 100° to the central axis 101. Then, at the mid-body portion 124, the anterior flaps 120a-b have a bend that defines an angle θ in a range of between 20° to 60°, or 30° to 60°, or 30° to 70°, or 40° to 60°, or 40° to 70°, or 40° to 50°, without limitation.

The bends in the mid-body 106 of the anterior flaps 120a-b can allow the anterior flaps 120a-b to conform to the contours of the wall that defines the RVOT. Accordingly, the bent anterior flaps 120a-b can reduce the potential of the anterior flaps 120a-b to restrict blood flow through the RVOT in some cases.

FIGS. 36 and 37 show two additional views of another example embodiment of the valve 100. The depicted embodiment includes an opening 126a that is defined by the covering 104 located at a terminal end portion of the first anterior flap 120a. Additionally, the covering 104 on the second anterior flap 120b defines an opening 126b at a terminal end portion of the second anterior flap 120b.

The openings 126a-b in the end portions of the anterior flaps 120a-b allow blood to flow through the anterior flaps 120a-b (via the openings 126a-b). This can be beneficial because in some implementations the anterior flaps 120a-b extend into the RVOT. Accordingly, such openings 126a-b may in some cases reduce the potential of the anterior flaps 120a-b to restrict blood flow through the RVOT.

FIG. 39 schematically illustrates an annulus 12 of a typical tricuspid valve 10. The shape of the annulus 12 of many tricuspid valves 10 is not circular. Often, as depicted here, shape of the annulus 12 is oblong or ovoidal (oval shaped). That is, the distance between the posterior and anterior regions of the annulus 12 is longer than the distance between the septal and lateral regions of the annulus 12. Accordingly, it can be said that the annulus 12 defines a major diameter 16 between the posterior and anterior regions, and a minor diameter 18 between the septal and lateral regions of the annulus 12.

FIG. 40 schematically illustrates an example embodiment of the valve 100 implanted in the annulus 12 of the typical tricuspid valve 10. In this embodiment of the valve 100, the main body 106 has an ovular outer cross-sectional shape. In contrast, the occluder 110 within the main body 106 has a circular cross-sectional shape.

The oval shaped main body 106 of the valve 100 has a major diameter 108 and a minor diameter 109. The anterior flaps 120a-b and the posterior flap 130 extend from the main body 106 along a direction that is transverse to the major diameter 108 of the oval shaped main body 106. In some embodiments, the anterior flaps 120a-b and/or the posterior flap 130 extend from the main body 106 substantially orthogonally or perpendicularly (e.g., 90°+/−59, 90°+/−10°, 90°+/−15°, or 90°+/−20°) to the major diameter 108 of the oval shaped main body 106. In some embodiments, the valve 100 can also include one or more leaflet engagement members 140 (e.g., refer to FIG. 16-23) that extend along a direction that is transverse (or substantially orthogonal) to the major diameter 108 of the oval shaped main body 106 in the same direction as the posterior flap 130.

In some embodiments, as depicted in FIG. 40, the main body 106 is smaller than the full size/area of the annulus 12. Accordingly, the anterior flaps 120a-b can be used to fill up the internal area defined the annulus 12 that is not occupied by the main body 106. The occluder 110 occupies a circular cross-sectional shape that is smaller than the main body 106, which is adequate for the hemodynamics of the blood flow between the atrium and the ventricle. In some embodiments, the percentage of the internal area defined by the annulus 12 that is occupied by the main body 106 is about 50% (with the remaining about 50% of the area of the annulus 12 being covered by the anterior flaps 120a-b). In some embodiments, the percentage of the area of the annulus 12 that is occupied by the main body 106 is in a range of about 50% to 60%, or 55% to 65%, or 60%, to 70%, or 65% to 75%, or 70% to 80%, or 75% to 85%, or 60% to 80%, without limitation, with the anterior flaps 120a-b covering the remainder of the area of the annulus 12. In some embodiments, the anterior flaps 120a-b cover at least 50%, or at least 40%, or at least 30%, or at least 20%, or at least 10%, or at least 5% of the internal area defined by the annulus 12.

The fact that the anterior flaps 120a-b cover at least a portion of the area of the annulus 12 can be beneficial for additional reasons. For example, if, at some point in the future after the valve 100 has been implanted in the annulus 12, a pacemaker lead needs to be passed through the annulus 12, then a location on the anterior flaps 120a-b can be punctured to allow the pacemaker lead to pass through the anterior flaps 120a-b. The puncture can be at the open passage 122, or at another location of the anterior flaps 120a-b. The ability to pass a pacemaker lead through the anterior flaps 120a-b is advantageous because doing so does not affect the functionality of the occluder 110. This is advantage is made possible by the fact that the anterior flaps 120a-b cover at least a portion of the area of the annulus 12.

Since, as depicted in the example of FIG. 40, in some cases a portion of the oval shaped annulus 12 is covered by the anterior flaps 120a-b, the main body 106 need not be circular, and can be constructed to have various types of cross-sectional shapes. An oval shape (as shown) may be preferable in some cases, as it can be radially compressed well for fitting in a low-profile delivery catheter because it can have a smaller perimeter due to the minor diameter 109 of the main body 106 being shorter than the major diameter 108. If, for example, the main body 106 had a circular cross-sectional shape with a diameter equal to the major diameter 108, the main body 106 could not be radially crushed/compressed to as small of a size as the depicted oval shaped main body 106. Hence, a larger delivery sheath would be required if the main body 106 was circular (as compared to ovular as shown).

Interestingly, in the example depicted in FIG. 40, while both the annulus 12 of the tricuspid valve 10 and the main body 106 of the valve 100 are oblong or oval shaped, the orientations of their major and minor diameters are about 90° (e.g., 90°+/−10°) offset in relation to each other when the valve 100 is implanted in the tricuspid valve 10. That is, the major diameter 108 of the oval shaped main body 106 is substantially parallel (e.g., +/−10°) relative to the minor diameter 18 of the annulus 12. Moreover, the minor diameter 109 of the oval shaped main body 106 is substantially parallel (e.g., +/−10°) relative to the major diameter 16 of the annulus 12. These geometric relationships are beneficial because the annulus 12 is fully occluded by the valve 100 and the diameter of the radially compressed delivery configuration of the valve 100 can be reduced (as compared to having the main body 106 filling a larger area of the annulus 12).

Again, it is evident in FIG. 40 that the opening defined by the native annulus 12 is not completely filled by the main body 106. Instead, the laterally-extending first and second anterior flaps 120a-b help to cover and fluidly seal the native tricuspid valve opening which is not circular in this example (e.g., with the native valve opening being oblong, or irregularly shaped). In other words, in combination with the main body 106 of the valve 100, the first and second anterior flaps 120a-b (and the laterally-extending posterior anchoring flap 130 in some cases) help to cover and fluidly seal the native tricuspid valve opening which is not circular in some cases. In addition, terminal end portions of the first and second anterior flaps 120a-b extend into the RVOT to provide anchoring and migration resistance. Accordingly, the first and second anterior flaps 120a-b perform both sealing and anchorage.

The configuration of the valve 100 with its oval shaped main body 106 and its first and second anterior flaps 120a-b that extend along directions that are transverse to the major diameter 108 (e.g., substantially orthogonally) can be advantageous for multiple reasons. For example, as shown in FIG. 40, while the entirety of space within the native annulus 12 is occluded by the valve 100, a significant portion of the occlusion is provided by the first and second anterior flaps 120a-b. This is advantageous because the first and second anterior flaps 120a-b can be radially compressed to a smaller delivery profile than the more substantial frame 102 of the main body 106. That is the case because the first and second anterior flaps 120a-b have fewer components of the frame 102 than the main body 106. In addition, as shown in FIGS.

24-26, the first and second anterior flaps 120*a-b* can be longitudinally spaced away from the main body 106 when collapsed in the delivery catheter/sheath 200. Since these portions are not radially "stacked" together in the delivery catheter/sheath 200, this facilitates their ability to be compressed into a smaller delivery catheter/sheath 200.

Hence, for at least the reasons described above, the valve 100 can be advantageously delivered and deployed via a smaller diameter delivery catheter/sheath as a result of the depicted design of the valve 100. In addition, the oval shaped main body 106 (with its minor diameter 109) has a smaller outer periphery (e.g., as compared to if the main body 106 was made with a circular cross-section having a diameter equal to its major diameter 108). The comparative reduction in the bulk of the frame 102 of the main body 106 enables the valve 100 to be radially compressed to a smaller delivery profile. This is another structural reason that allows the valve 100 to be advantageously delivered and deployed via a smaller diameter delivery sheath/catheter as a result of the depicted design of the valve 100.

In some cases, the shape of a patient's native annulus 12 is generally circular. In such a case, the valve 100 can still provide much of the benefits described above. For example, the main body 106 can still have an ovular outer cross-sectional shape that occupies less than the full circular area of the native annulus 12 (with the first and second anterior flaps 120*a-b* occupying the remainder). In that case, the valve 100 is implanted in the native annulus 12 such that the central axis 101 of the occluder 110 is laterally offset (e.g., in the posterior direction) from the geometric center of the generally circular native annulus 12. In addition, the major diameter 108 of the main body 106 can be shorter than the diameter of the native annulus 12. For example, in some embodiments the length of the major diameter 108 of the main body 106 is about 60% to 80% of the diameter of the native annulus 12, or about 70% to 90% of the diameter of the native annulus 12, or about 80% to 95% of the diameter of the native annulus 12, without limitation.

Figure 41:
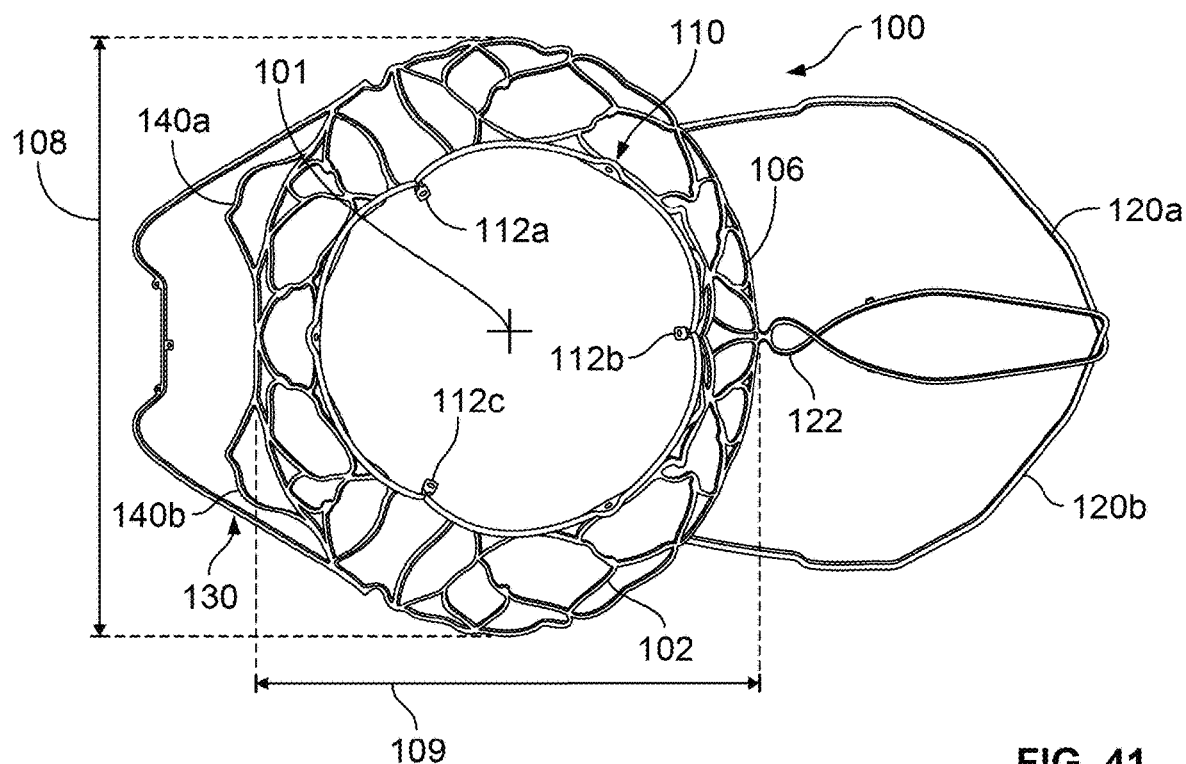
FIG. 41 is a top view of a frame of an example prosthetic heart valve that is configured like the schematic example of FIG. 40.

FIG. 41 illustrates a frame 102 that is shaped like the frame of the schematically depicted valve 100 of FIG. 40. The illustrated frame 102 has the main body 106 with the oval shaped outer profile. The oval shaped outer profile defines the major diameter 108 and the minor diameter 109. The occluder 110 has a circular cross-sectional shape.

Figure 42:
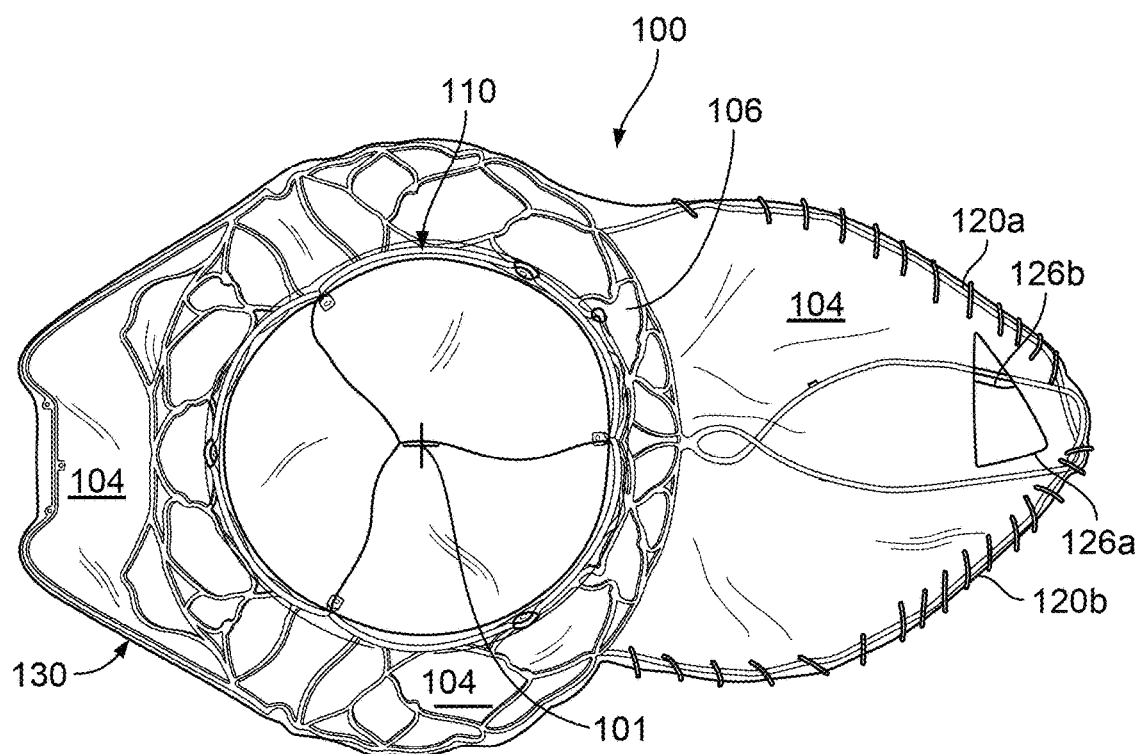
FIG. 42 shows a top view of an example prosthetic heart valve that includes the frame of FIG. 41.

FIG. 42 shows a covering 104 on the frame 102 of FIG. 41. The openings 126*a-b* in the end portions of the anterior flaps 120*a-b* are also shown. It can be seen that, in some embodiments, at least some portions of the openings 126*a-b* align and overlap each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Although a number of implementations have been described in detail above, other modifications are possible. For example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A prosthetic heart valve comprising:
   a main body comprising an inflow end portion and an outflow end portion;
   an occluder extending between the inflow end and outflow end portions, the occluder defining an inlet opening and a longitudinal axis, the occluder comprising valve leaflets attached to the main body in an arrangement that: (i) allows blood flow through the occluder in a downward direction from the inflow end portion toward the outflow end portion and (ii) prevents blood flow through the occluder in an upward direction from the outflow end portion toward the inflow end portion; and
   a posterior flap extending transversely away from the outflow end portion of the main body,
   wherein the posterior flap comprises:
      a first portion attached to the main body and comprising a portion that extends away from the main body and in the upward direction; and
      a second portion extending from the first portion and in the downward direction such that an angle is defined between the first and second portions, wherein the second portion comprises a wire loop that extends from the first portion, and wherein the second portion extends in the downward direction to a location below where the first portion is attached to the main body.

2. The prosthetic heart valve of claim 1, further comprising a first anterior flap and a second anterior flap extending away from the outflow end portion of the main body, wherein portions of the first anterior flap and the second anterior flap are configured to overlap each other when the prosthetic heart valve is deployed.

3. The prosthetic heart valve of claim 2, wherein an open space is defined between the first anterior flap and the second anterior flap when the prosthetic heart valve is deployed.

4. The prosthetic heart valve of claim 2, wherein the first and second anterior flaps each include a mid-body portion that is bent at an angle that directs terminal end portions of each of the first and second anterior flaps partially toward the inflow end portion.

5. The prosthetic heart valve of claim 4, wherein the angle of the mid-body portion of the first and second anterior flaps is between 20° and 60°.

6. The prosthetic heart valve of claim 2, further comprising a covering attached to the first and second anterior flaps, wherein the covering defines a first opening through a terminal end portion of the first anterior flap, and wherein the covering defines a second opening through a terminal end portion of the second anterior flap.

7. The prosthetic heart valve of claim 2, wherein the first and second anterior flaps extend farther away from the longitudinal axis than the posterior flap.

8. The prosthetic heart valve of claim 1, wherein the angle defined between the first and second portions of the posterior flap is in a range of 40° to 140°.

9. The prosthetic heart valve of claim 1, wherein the angle defined between the first and second portions of the posterior flap is in a range of 60° to 120°.

10. The prosthetic heart valve of claim 1, wherein the angle defined between the first and second portions of the posterior flap is in a range of 80° to 100°.

11. The prosthetic heart valve of claim 1, further comprising a covering material on the posterior flap.

12. A prosthetic heart valve comprising:
   a main body comprising an inflow end portion and an outflow end portion;
   an occluder extending between the inflow end and outflow end portions, the occluder defining an inlet opening and a longitudinal axis, the occluder comprising valve leaflets attached to the main body in an arrangement that: (i) allows blood flow through the occluder in a downward direction from the inflow end portion toward the outflow end portion and (ii) prevents blood flow through the occluder in an upward direction from the outflow end portion toward the inflow end portion;
   a posterior flap extending transversely away from the outflow end portion of the main body,
   wherein the posterior flap comprises:
      a first portion attached to the main body and comprising a portion that extends away from the main body and in the upward direction; and
      a second portion extending from the first portion and in the downward direction such that an angle is defined between the first and second portions; and
   a leaflet engagement member extending from the main body, a portion of the leaflet engagement member extending toward the inflow end portion and terminating at a free end, wherein the leaflet engagement member is a U-shaped wire loop.

13. The prosthetic heart valve of claim 12, wherein the posterior flap extends farther away from the main body than the leaflet engagement member.

14. The prosthetic heart valve of claim 12, wherein an area of the main body that the leaflet engagement member extends from is the outflow end portion or a mid-body portion located between the inflow end and outflow end portions.

15. The prosthetic heart valve of claim 12, wherein the angle defined between the first and second portions of the posterior flap is in a range of 40° to 140°.

16. The prosthetic heart valve of claim 12, wherein the angle defined between the first and second portions of the posterior flap is in a range of 60° to 120°.

17. The prosthetic heart valve of claim 12, wherein the angle defined between the first and second portions of the posterior flap is in a range of 80° to 100°.

18. The prosthetic heart valve of claim 12, further comprising a covering material on the posterior flap.

* * * * *